United States Patent
Hatakeyama

(10) Patent No.: US 10,610,188 B2
(45) Date of Patent: Apr. 7, 2020

(54) X-RAY IMAGING CONDITION MODIFICATION METHOD AND X-RAY SYSTEM

(71) Applicant: Norihito Hatakeyama, Osaka (JP)

(72) Inventor: Norihito Hatakeyama, Osaka (JP)

(*) Notice: Subject to any disclaimer, the term of this patent is extended or adjusted under 35 U.S.C. 154(b) by 323 days.

(21) Appl. No.: 15/617,527

(22) Filed: Jun. 8, 2017

(65) Prior Publication Data
US 2018/0199907 A1    Jul. 19, 2018

(30) Foreign Application Priority Data
Jan. 18, 2017    (JP) ................. 2017-006982

(51) Int. Cl.
| | | |
|---|---|---|
| A61B 6/00 | (2006.01) | |
| H05G 1/26 | (2006.01) | |
| H05G 1/30 | (2006.01) | |
| H05G 1/32 | (2006.01) | |
| H05G 1/34 | (2006.01) | |
| H05G 1/38 | (2006.01) | |

(52) U.S. Cl.
CPC ............ *A61B 6/545* (2013.01); *A61B 6/52* (2013.01); *A61B 6/5205* (2013.01); *A61B 6/5258* (2013.01); *A61B 6/5294* (2013.01); *A61B 6/54* (2013.01); *A61B 6/542* (2013.01); *A61B 6/544* (2013.01); *A61B 6/58* (2013.01); *A61B 6/588* (2013.01); *A61B 6/589* (2013.01); *H05G 1/26* (2013.01); *H05G 1/30* (2013.01); *H05G 1/32* (2013.01); *H05G 1/34* (2013.01); *H05G 1/38* (2013.01)

(58) Field of Classification Search
CPC ........... A61B 6/52; A61B 6/5294; A61B 6/54; A61B 6/542; A61B 6/545; A61B 6/588; A61B 6/589; H05G 1/26; H05G 1/30; H05G 1/32; H05G 1/34; H05G 1/38
USPC .................. 378/62, 98.7, 16, 91, 207
See application file for complete search history.

(56) References Cited

U.S. PATENT DOCUMENTS 5,661,774 A * 8/1997 Gordon ............... G01N 23/046
                                                        378/101
5,949,811 A * 9/1999 Baba .................. A61B 6/4225
                                                        378/108

(Continued)

FOREIGN PATENT DOCUMENTS

| JP | 7-336597 | 12/1995 |
| JP | 2004-337199 | 12/2004 |

(Continued)

OTHER PUBLICATIONS

Masaru Uchida et al., "Houshasen Gijutsusha No Tameno Gazou Kogaku (Imaging technology for radiologists)", Tsusho sangyo kenkyu sha, co., 1978, p. 104-121 with partial English translation.

*Primary Examiner* — Allen C. Ho
(74) *Attorney, Agent, or Firm* — Wenderoth, Lind & Ponack, L.L.P.

(57) ABSTRACT

An x-ray imaging condition modification method includes modifying a first imaging condition to a second imaging condition by changing a value of at least one parameter among parameters included in the first imaging condition to an arbitrary value, and changing values of remaining parameters that are parameters other than the at least one parameter using the arbitrary value and an approximate function.

4 Claims, 11 Drawing Sheets

(56) References Cited

U.S. PATENT DOCUMENTS

| | | | | |
|---|---|---|---|---|
| 6,178,228 B1 | * | 1/2001 | Schol | G06F 3/04847 345/156 |
| 6,377,656 B1 | * | 4/2002 | Ueki | A61B 6/4225 378/98.7 |
| 6,404,848 B1 | * | 6/2002 | Ishisaka | A61B 6/032 378/62 |
| 6,901,129 B2 | * | 5/2005 | Tachizaki | A61B 6/032 378/4 |
| 6,920,201 B2 | * | 7/2005 | Maack | A61B 6/00 378/108 |
| 6,977,989 B2 | * | 12/2005 | Bothe | A61B 6/00 378/108 |
| 7,031,423 B2 | * | 4/2006 | Tsukagoshi | A61B 6/032 378/19 |
| 7,072,437 B2 | * | 7/2006 | Seto | A61B 6/032 378/162 |
| 7,103,139 B2 | * | 9/2006 | Nagaoka | A61B 6/032 378/16 |
| 7,203,270 B2 | * | 4/2007 | Okumura | A61B 6/032 378/109 |
| 7,215,733 B2 | * | 5/2007 | Nabatame | A61B 6/032 378/110 |
| 7,298,823 B2 | * | 11/2007 | Bernhardt | A61B 6/4035 378/97 |
| 7,431,500 B2 | * | 10/2008 | Deych | A61B 6/482 378/111 |
| 7,474,731 B2 | * | 1/2009 | Spahn | A61B 6/544 378/207 |
| 7,639,776 B2 | * | 12/2009 | Gohno | A61B 6/032 378/109 |
| 7,684,605 B2 | * | 3/2010 | Klingenbeck-Regn | A61B 6/00 378/62 |
| 7,715,522 B2 | * | 5/2010 | Goto | A61B 6/032 378/16 |
| 7,813,471 B2 | * | 10/2010 | Hirokawa | A61B 6/032 378/4 |
| 7,813,474 B2 | * | 10/2010 | Wu | A61B 6/032 378/16 |
| 7,826,587 B1 | * | 11/2010 | Langan | A61B 6/032 378/16 |
| 7,856,134 B2 | * | 12/2010 | Rührnschopf | A61B 6/032 382/128 |
| 7,970,098 B2 | * | 6/2011 | Haras | A61B 5/417 378/16 |
| 8,077,828 B2 | * | 12/2011 | Aoyama | A61B 6/465 378/108 |
| 8,194,824 B2 | * | 6/2012 | Takahashi | A61B 6/542 378/108 |
| 8,204,290 B2 | * | 6/2012 | Haras | A61B 6/032 382/131 |
| 8,781,062 B2 | * | 7/2014 | Besson | G01N 23/04 378/16 |
| 8,831,177 B2 | * | 9/2014 | Chung | A61B 6/5217 378/207 |
| 8,891,849 B2 | * | 11/2014 | Rohler | A61B 6/032 382/132 |
| 9,020,220 B2 | * | 4/2015 | Nukui | A61B 6/488 382/128 |
| 9,241,394 B2 | * | 1/2016 | Tanaka | H05G 1/30 |
| 9,254,107 B2 | * | 2/2016 | Sugaya | A61B 6/032 |
| 9,320,482 B2 | * | 4/2016 | Tajima | A61B 6/42 |
| 9,724,064 B2 | * | 8/2017 | Yabugami | A61B 5/1075 |
| 9,820,714 B2 | * | 11/2017 | Sugahara | A61B 6/502 |
| 9,844,357 B2 | * | 12/2017 | Lee | A61B 6/542 |
| 9,949,711 B2 | * | 4/2018 | Goto | A61B 6/542 |
| 9,968,307 B2 | * | 5/2018 | Stevens | A61B 6/032 |
| 9,984,306 B2 | * | 5/2018 | Han | G06K 9/4642 |
| 10,028,719 B1 | * | 7/2018 | Bernhardt | H05G 1/44 |
| 10,172,584 B2 | * | 1/2019 | Hatakeyama | A61B 6/4452 |
| 10,188,366 B2 | * | 1/2019 | Beak | A61B 6/4233 |
| 10,219,771 B2 | * | 3/2019 | Jung | A61B 6/032 |
| 10,383,583 B2 | * | 8/2019 | Tomomura | A61B 6/467 |
| 2009/0141854 A1 | | 6/2009 | Hirokawa et al. | |
| 2009/0279665 A1 | | 11/2009 | Takahashi | |

FOREIGN PATENT DOCUMENTS

| | | |
|---|---|---|
| JP | 2009-268827 | 11/2009 |
| WO | 2007/138979 | 12/2007 |

* cited by examiner

FIG. 9

| Converted value (cm) | k1 | k2 | k3 | k4 | k5 |
|---|---|---|---|---|---|
| 1 | 3.47 | 16.613 | 0.538 | 12.383 | 0.53 |
| 2 | 3.52 | 16.852 | 0.538 | 12.383 | 0.53 |
| 3 | 3.57 | 17.091 | 0.538 | 12.383 | 0.53 |
| 4 | 3.61 | 17.283 | 0.538 | 12.383 | 0.53 |
| 5 | 3.66 | 17.522 | 0.538 | 12.383 | 0.53 |
| 6 | 3.7 | 17.714 | 0.538 | 12.383 | 0.53 |
| 7 | 3.76 | 18.001 | 0.538 | 12.383 | 0.53 |
| 8 | 3.81 | 18.24 | 0.538 | 12.383 | 0.53 |
| 9 | 3.85 | 18.432 | 0.538 | 12.383 | 0.53 |
| 10 | 3.91 | 18.719 | 0.538 | 12.383 | 0.53 |
| 11 | 3.95 | 18.911 | 0.538 | 12.383 | 0.53 |
| 12 | 4.0 | 19.15 | 0.538 | 12.383 | 0.53 |
| 13 | 4.05 | 19.389 | 0.538 | 12.383 | 0.53 |
| 14 | 4.09 | 19.581 | 0.538 | 12.383 | 0.53 |
| 15 | 4.15 | 19.868 | 0.538 | 12.383 | 0.53 |
| 16 | 4.19 | 20.06 | 0.538 | 12.383 | 0.53 |
| 17 | 4.25 | 20.347 | 0.538 | 12.383 | 0.53 |
| 18 | 4.3 | 20.586 | 0.538 | 12.383 | 0.53 |
| 19 | 4.34 | 20.778 | 0.538 | 12.383 | 0.53 |
| 20 | 4.4 | 21.065 | 0.538 | 12.383 | 0.53 |
| 21 | 4.46 | 21.352 | 0.538 | 12.383 | 0.53 |
| 22 | 4.5 | 21.544 | 0.538 | 12.383 | 0.53 |
| 23 | 4.55 | 21.783 | 0.538 | 12.383 | 0.53 |
| 24 | 4.59 | 21.975 | 0.538 | 12.383 | 0.53 |
| 25 | 4.65 | 22.262 | 0.538 | 12.383 | 0.53 |

FIG. 11

|  | Tube voltage (kVp) | Tube current (mA) | Imaging time (sec) | Imaging distance SID (cm) |
|---|---|---|---|---|
| Condition 1 | 122 | 100 | 0.045 | 200 |
| Condition 2 | 127 | 200 | 0.020 | 200 |
| Condition 3 | 117 | 250 | 0.012 | 150 |
| Condition 4 | 86 | 320 | 0.032 | 150 |
| Condition 5 | 77 | 400 | 0.040 | 157 |
| Condition 6 | 85 | 320 | 0.032 | 150 |

X-RAY IMAGING CONDITION MODIFICATION METHOD AND X-RAY SYSTEM

CROSS REFERENCE TO RELATED APPLICATION

The present application is based on and claims priority of Japanese Patent Application No. 2017-006982 filed on Jan. 18, 2017. The entire disclosure of the above-identified application, including the specification, drawings and claims is incorporated herein by reference in its entirety.

FIELD

The present disclosure relates to an x-ray imaging condition modification method and an x-ray system for modifying an imaging condition under which an x-ray image is obtained using x-rays emitted from an x-ray tube.

BACKGROUND

There are roughly two conventional methods for obtaining a medical x-ray image.

With the first conventional method, the person capturing an x-ray image (hereinafter referred to as an image-capturing person) stores in advance for each configuration of the x-ray system and for each examined body part to be imaged, an imaging condition under which an x-ray image of a body meeting a predetermined standard (a standard predetermined based on the height, the weight, the chest and hip thicknesses, the race, and the age, for example) (the body meeting the predetermined standard is hereinafter referred to as a standard body) has an appropriate radiographic effect, in memory included in the x-ray system. It should be noted that examples of parameters of the imaging condition include an x-ray tube voltage (hereinafter referred to as a tube voltage), an x-ray tube current (hereinafter referred to as a tube current), an imaging time, and an imaging distance. In the case of analog x-ray images, the x-ray image having an appropriate radiographic effect (also referred to as an appropriate x-ray image) refers to an image having a radiographic density of about 1.0 in the examined body part, for example. In the case of digital x-ray images, the appropriate x-ray image refers to an image having an exposure index (EI) value corresponding to the image quality of the analog x-ray image. Then, the image-capturing person compares the standard body and the examinee's body in terms of the thickness and the body build, for example, and when there is a difference in the thickness and/or the body build, modifies the predetermined standard-body imaging condition based on an imaging condition modification method such as an exponential method, and captures an image of the examinee's body using the modified imaging condition.

With the second conventional method, the image-capturing person determines, for each thickness of the examinee's body and each examined body part, the tube voltage and the tube current to be used, and irradiates the examined body part with x-rays. Then, while irradiating the examined body part with x-rays, the image-capturing person measures the dosage of x-rays passing through the examinee's body and captures an image of the examinee's body using an automatic exposure control (AEC) mechanism that blocks the x-ray irradiation when the dosage of the x-rays passing through the examinee's body reaches a predetermined x-ray dosage.

With the first image obtaining method, the imaging condition for the standard body is subjected to primary modification according to the thickness and the body build of the examinee's body. Furthermore, the imaging condition obtained by the primary modification is subjected to secondary modification in consideration of a motion of the examined body part and a magnification ratio that is dependent on the geometric position of the examined body part. As a result of such primary modification and secondary modification, an appropriate image is obtained. Therefore, for example, when the examined body part moves, image capturing is attempted under, as an imaging condition obtained by the secondary modification (hereinafter referred to as a secondarily modified condition), an imaging condition including a greater tube voltage, a greater tube current, and a shorter imaging time than the imaging condition obtained by the primary modification (hereinafter referred to as a primarily modified condition). Furthermore, for example, when the magnification ratio increases, image capturing is attempted using an x-ray tube having a small focal spot under, as the secondarily modified condition, an imaging condition including a tube current smaller than a tube current used for an x-ray tube having a large focal spot. However, at the time of the primary modification and the secondary modification, there are a large number of imaging conditions that give an analog image an equivalent radiographic density in the case of analog image capturing or a large number of imaging conditions that give an x-ray detector system an equivalent irradiation dose factor (hereinafter also referred to as EI-equivalent imaging conditions) in the case of digital image capturing. It should be noted that the imaging conditions that give an analog image an equivalent radiographic density and the EI-equivalent imaging conditions are hereinafter also collectively referred to as equivalent radiographic effect conditions.

As compared to the first image obtaining method, the second image obtaining method allows capturing an image of the examinee's body with a simple operation technique using the AEC mechanism. However, since the AEC mechanism does not take into consideration such a factor as a motion of the examined body part or the magnification ratio dependent on the geometric positional relationship of the examined body part, it may not be always possible to obtain an image appropriate for medical practice. Although the second image obtaining method makes it possible to obtain an appropriate image if a motion of the examined body part and the magnification ratio dependent on the geometric position of the examined body part are taken into consideration, experience and knowledge are required.

With the first image obtaining method, if a part of the parameters included in the imaging condition, that is, the tube voltage, the tube current, the imaging time, and the imaging distance, for example, is changed, it is also necessary to change the remaining parameters in order to obtain an equivalent radiographic effect condition, even if there is no change to the configuration of the x-ray system. A change of a parameter including a change of the tube voltage is particularly difficult. To address this difficulty, various imaging condition modification methods for efficiently changing (modifying) the imaging condition are publicly available.

Non-Patent Literature 1 (NPL 1) discloses some examples of such imaging condition modification methods.

Specifically, NPL 1 describes a method using an exponential function as one of the various imaging condition modification methods.

CITATION LIST

Non Patent Literature

[NPL 1] Masaru Uchida, Kazuya Yamashita, and Hiroshi Inatsu, "Houshasen gijutsusha no tameno gazou kogaku" (Imaging technology for radiologists), Tsusho sangyo kenkyu sha, co. 1978

SUMMARY

Technical Problem

With the conventional exponential method disclosed in NPL 1, however, a tube voltage coefficient table (FIG. 7 to be described later) is prepared for each configuration of the x-ray system, and when the tube voltage needs to be changed, the image-capturing person refers to the table and changes the tube voltage to a new tube voltage. This means that, the image-capturing person needs to refer to the table every time he/she makes such a change to the imaging condition that involves a change to the tube voltage, thus making the process extremely inefficient. Moreover, since a roughly calculated value or a round figure is used for convenience as the exponential of the exponential function used for preparing the table, such a roughly calculated exponent causes an error in an exponential operation to increase exponentially. Thus, such a conventional method has been impractical for actual x-ray imaging.

In view of the above circumstances, it is an object of the present disclosure to provide an x-ray imaging condition modification method and an x-ray system for easily modifying a first imaging condition to a second imaging condition under which an x-ray image having a radiographic effect equivalent to a radiographic effect of an x-ray image obtained under the first imaging condition is obtained.

Solution to Problem

An x-ray imaging condition modification method according to an aspect of the present disclosure is an x-ray imaging condition modification method for modifying an imaging condition to obtain an x-ray image having an appropriate radiographic effect using x-rays emitted from an x-ray tube, the imaging condition including, as parameters, at least (i) a tube voltage, (ii-1) a tube current and an imaging time or (ii-2) a mAs value which is a product of the tube current and the imaging time, and (iii) an imaging distance between a focal spot of the x-ray tube and an x-ray detector system, the method including modifying a first imaging condition to a second imaging condition by changing a value of at least one parameter among the parameters included in the first imaging condition to an arbitrary value, and changing values of remaining parameters that are parameters other than the at least one parameter using the arbitrary value and an approximate function, the second imaging condition being an imaging condition under which an x-ray image having a radiographic effect equivalent to a radiographic effect of an x-ray image obtained under the first imaging condition is obtained, wherein the approximate function is for approximating to a curve obtained by plotting, for each of a plurality of imaging conditions, a relationship between a new tube voltage included in each of the plurality of imaging conditions and a mAs value coefficient Q represented by Equation 22, where $i2$, $t2$, and $r2$ represent a new tube current, a new imaging time, and a new imaging distance, respectively, which are included in the plurality of imaging conditions, and $i1$, $t1$, and $r1$ represent the tube current, the imaging time, and the imaging distance, respectively, which are included in the first imaging condition, the plurality of imaging conditions being determined through an experiment so as to obtain the x-ray image having the radiographic effect equivalent to the radiographic effect of the x-ray image obtained under the first imaging condition.

An x-ray system according to an aspect of the present disclosure is an x-ray system including: a computer that performs the x-ray imaging condition modification method described above; a high-voltage generation device that generates a tube voltage and a mAs value that correspond to the second imaging condition obtained by modification performed by the computer; an x-ray tube that emits x-rays at the tube voltage and the mAs value supplied from the high-voltage generation device; and an x-ray detector system that detects the x-rays emitted from the x-ray tube.

Advantageous Effects

With the x-ray imaging condition modification method and the x-ray system according to the present disclosure, it is possible to easily modify a first imaging condition to a second imaging condition under which an x-ray image having a radiographic effect equivalent to a radiographic effect of an x-ray image obtained under the first imaging condition is obtained.

BRIEF DESCRIPTION OF DRAWINGS

These and other objects, advantages and features of the invention will become apparent from the following description thereof taken in conjunction with the accompanying drawings that illustrate a specific embodiment of the present disclosure.

FIG. 9 is an example of a database which is prepared in advance for each configuration of an x-ray system and for each examined body part, and which associates a converted value with k1 to k5 included in an approximate function.

FIG. 11 is a diagram illustrating examples of a second imaging condition obtained by modification performed by a modification unit according to an embodiment.

Figure 1:
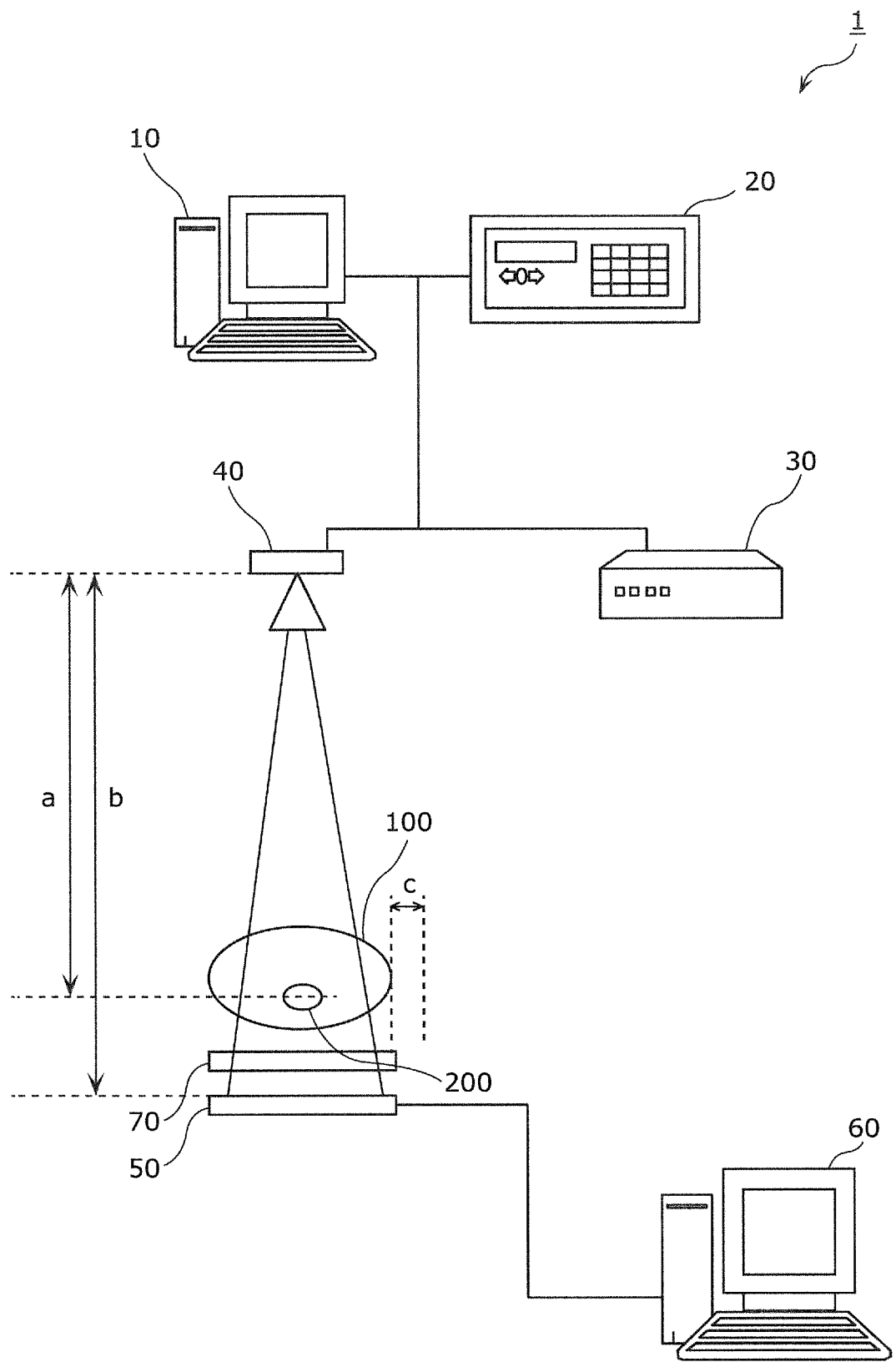
FIG. 1 is a diagram illustrating an example of the entire configuration of an x-ray system according to an embodiment.

DESCRIPTION OF EMBODIMENT (Circumstances that Resulted in an Aspect of the Present Disclosure)

An experimental relational expression between a radiographic effect that gives a radiographic density to the film and various factors (imaging condition) for forming an image is known as in the following Equation 1.

[Math. 1]

$$E = W \frac{V^n itsfZ}{r^2 BG} e^{-ud} \quad \text{(Equation 1)}$$

Here, E represents a radiographic effect given to the film, W represents a constant, V represents a tube voltage (kVp), i represents a tube current (mA), t represents an imaging time (sec), s represents an intensifying factor (coefficient) for an intensifying screen, f represents a film sensitivity, Z represents the atomic number of a focal spot structural substance, u represents an attenuation coefficient of the examinee's body, d represents the thickness (cm) of the examinee's body, r represents an imaging distance (cm) between the focal spot of the x-ray tube and the x-ray detector system (focus-film distance), B represents an exposure magnifying factor for an anti-scatter device, G represents a factor related to the irradiation field size, and n represents a power that is calculated through an experiment and is peculiar to the tube voltage.

When capturing the same examinee's body using the same x-ray system configuration brings about the same radiographic effect, the following Equation 2 holds for the radiographic effect under two imaging conditions.

[Math. 2]

$$E = W \frac{(V1)^{n1}(i1)(t1)sfZ}{(r1)^2 BG} e^{-ud} = W \frac{(V2)^{n2}(i2)(t2)sfZ}{(r2)^2 BG} e^{-ud} \quad \text{(Equation 2)}$$

Here, V1, i1, t1, r1, and n1 represent the tube voltage, the tube current, the imaging time, the focus-film distance, and the power peculiar to the tube voltage, respectively, which are included in an imaging condition before change (for example, a first imaging condition that is to be described later) among the imaging condition before change and an imaging condition after change. Furthermore, V2, i2, t2, r2, and n2 represent a new tube voltage, a new tube current, a new imaging time, a new focus-film distance (a new imaging distance), and a power peculiar to the new tube voltage, respectively, which are included in the imaging condition after change (for example, a second imaging condition that is to be described later). It should be noted that the parameters of the imaging condition include at least (i) the tube voltage, (ii-1) the tube current and the imaging time or (ii-2) a mAs value which is a product of the tube current and the imaging time, and (iii) the imaging distance between the focal spot of the x-ray tube and the x-ray detector system. The parameters for the imaging condition need not include the mAs value if the tube current and the imaging time are included, and need not include the tube current and the imaging time if the mAs value is included.

Summarizing Equation 2 gives the following Equation 3.

[Math. 3]

$$\frac{(V1)^{n1}(i1)(t1)}{(r1)^2} = \frac{(V2)^{n2}(i2)(t2)}{(r2)^2} \quad \text{(Equation 3)}$$

Equation 3 indicates, for example, that in the case where the focus-film distance (hereinafter referred to as a source-image distance (SID)) included in the imaging condition is the same before and after the imaging condition is changed but the remaining parameters are changed, it is possible to obtain an equivalent radiographic effect by decreasing at least one of the tube current and the imaging time when, for example, the tube voltage is increased. Even when the same SID is used before and after the imaging condition is changed, there is a great number of imaging conditions after change, under which Equation 3 holds. When the SID does change, there is an almost infinite number of imaging conditions under which Equation 3 holds.

Moreover, when it is assumed that Equation 3 for achieving an equivalent radiographic effect before and after the imaging condition is changed holds also for a digital detector system, Equation 3 can be applied also to the EI value that is a unit of display of the irradiation dose factor for the digital detector system. With this, the number of EI-equivalent imaging conditions is also almost infinite.

As described above, even when a parameter such as the SID is restricted, there is a great number of combinations of the remaining parameters. Thus, the image-capturing person finds it hard to choose an appropriate combination when changing the imaging condition.

In view of this, when the parameters in Equation 3 are partially changed, the values of the remaining parameters are calculated through high-speed computation using a computer, so as to increase the efficiency of the modification of the imaging condition (equivalent radiographic effect condition) under which an equivalent radiographic density is obtained in the case of an analog image and under which an equivalent EI value is obtained in the case of a digital image.

Hereinafter, an x-ray imaging condition modification method and an x-ray system according to an embodiment of the present disclosure will be described in detail with reference to the drawings. It should be noted that the embodiment described below shows a specific example of the present disclosure. Therefore, the numerical values, structural elements, the arrangement and connection of the structural elements, steps, and the processing order of the steps, etc., shown in the following embodiment are mere examples, and are not intended to limit the present disclosure. As such, among the structural elements in the following embodiment, those not recited in any one of the independent claims indicating the broadest inventive concepts will be described as arbitrary structural elements.

It should also be noted that each figure is a schematic diagram and not necessarily a precise illustration.

(Embodiment)

FIG. 1 is a diagram illustrating an entire configuration of an x-ray system 1 according to an embodiment.

The x-ray system 1 is a system for obtaining an x-ray image of a body part of an examinee's body to be imaged for examination, and includes a computer 10, an operation panel 20, a high-voltage generation device 30, an x-ray tube 40, an x-ray detector system 50, a display device 60, and an anti-scatter device 70. FIG. 1 also illustrates, as an example, an examinee's body 100 and an examined body part 200 that is a part of the examinee's body 100.

The computer 10 executes a program for modifying a first imaging condition under which an x-ray image having an appropriate radiographic effect is obtained to a second imaging condition under which a radiographic effect equivalent to the radiographic effect of the x-ray image is achieved (hereinafter referred to as a program). The computer 10 will be described in detail with reference to FIG. 2 and FIG. 3 which are to be described later.

The operation panel 20 is a panel that receives an operation by the image-capturing person, and receives, for example, an operation for selecting a configuration of the x-ray system. Selecting a configuration of the x-ray system means selecting the presence or the absence of the anti-scatter device 70, selecting the type of the anti-scatter device 70, and selecting the type of the x-ray detector system 50. The operation panel 20 also receives, for example, an operation for selecting the type of the examined body part. Selecting the type of the examined body part means selecting whether the examined body part to be imaged is the chest or the abdomen, for example. Moreover, the operation panel 20 receives, for example, a distance b (an SID) between a focal spot of the x-ray tube 40 (hereinafter referred to as a tube focal spot) and the x-ray detector system 50. It should be noted that the operation panel 20 may include a display unit that displays the information received by the operation panel 20. The operation panel 20 may also be included in the computer 10, and a display unit included in the computer 10 may display the information received by the operation panel 20.

The high-voltage generation device 30 is a device for supplying the x-ray tube 40 with a high voltage and a DC current. The high-voltage generation device 30 generates a tube voltage and a mAs value corresponding to the second imaging condition obtained by the modification performed by the computer 10, and supplies the x-ray tube 40 with the tube voltage and the mAs value generated.

The x-ray tube 40 is a device that emits x-rays corresponding to the tube voltage and the mAs value supplied by the high-voltage generation device 30, and has two focal spots, namely, a small focal spot (nominal focal spot value: 0.6 mm) and a large focal spot (nominal focal spot value: 1.2 mm). The small focal spot and the large focal spot are switched according to the purpose. For example, the large focal spot is used when a large tube current (from 160 mA to 400 mA approximately, for example) is supplied, whereas the small focal spot is used when a small tube current (from 50 mA to 100 mA approximately, for example) is supplied. In terms of image capturing, the large focal spot is generally used for short-time imaging, whereas the small focal spot is generally used when capturing an enlarged or sharp image.

The x-ray detector system 50 detects x-rays passing though the examinee's body 100 (the examined body part 200). The x-ray detector system 50 is, for example, a combination of a film and an intensifying screen in the case of an analog x-ray detector system, whereas the x-ray detector system 50 is, for example, a flat panel detector in the case of a digital x-ray detector system.

The display device 60 displays an x-ray image showing the x-rays detected by the x-ray detector system 50. It should be noted that the display unit included in the computer 10 may display the x-ray image showing the x-rays detected by the x-ray detector system 50. The display unit in the following description may be any one of the display device 60, the display unit included in the computer 10, and the display unit included in the operation panel 20.

The anti-scatter device 70 eliminates scattering rays caused by the examinee's body (the examined body part) and is a part of the x-ray system 1. The anti-scatter device 70 is a 10:1 anti-scatter device for 120 kVp, for example. Depending on such factors as the type and the imaging direction of the examined body part, more than one type of anti-scatter device 70 can be set in the x-ray system. It should be noted that the anti-scatter device 70 need not be set in the x-ray system 1. In other words, the x-ray system 1 need not include the anti-scatter device 70.

Distance a represents the distance between the x-ray tube focal spot and the examined body part 200 plane (source-object distance (SOD)). Distance b represents the distance between the x-ray tube focal spot and the x-ray detector system 50 plane (SID). Distance c represents the outward amount of motion of the examinee's body 100 on a plane perpendicular to the x-ray incident direction and including the examined body part 200.

Next, the details of the computer 10 will be described with reference to FIG. 2 and FIG. 3.

Figure 2:
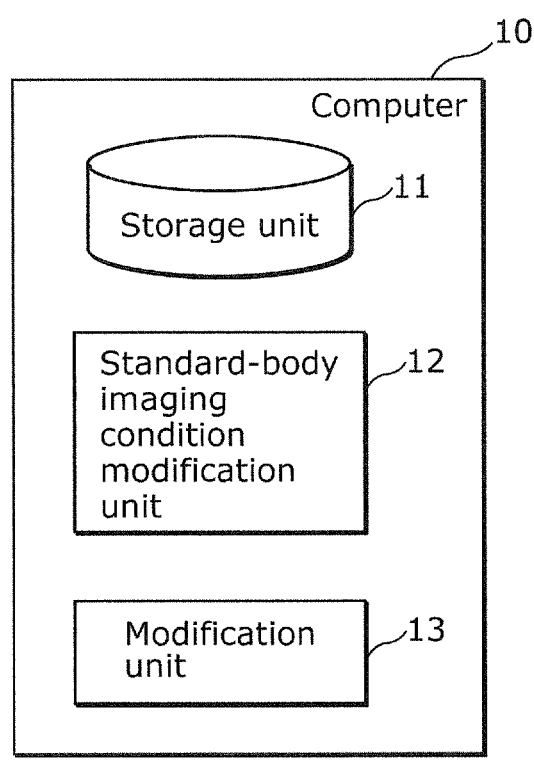
FIG. 2 is a block diagram illustrating an example of functions of a computer according to an embodiment.

FIG. 2 is a block diagram illustrating an example of functions of the computer 10 according to an embodiment.

Figure 3:
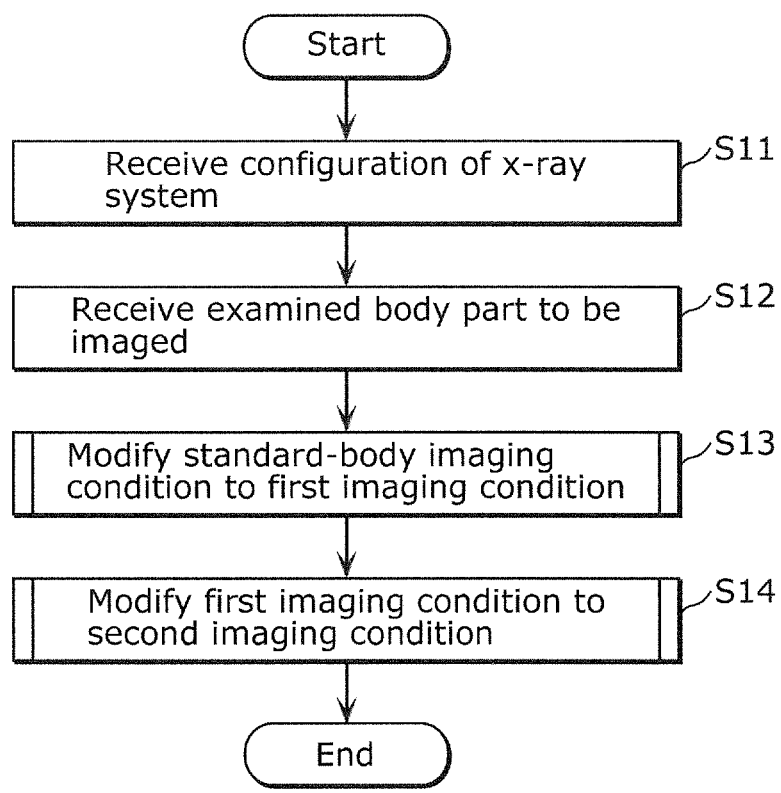
FIG. 3 is a flow chart illustrating an example of operations of a computer according to an embodiment.

FIG. 3 is a flow chart illustrating an example of operations of the computer 10 according to an embodiment.

The computer 10 includes a storage unit 11, a standard-body imaging condition modification unit 12, and a modification unit 13.

The storage unit 11 stores a program to be executed by the computer 10. The computer 10 operates based on the program stored in the storage unit 11. Specific operations of the computer 10 are performed by the standard-body imaging condition modification unit 12 and the modification unit 13, for example. Although the standard-body imaging condition modification unit 12 and the modification unit 13 are realized by, for example, a processor that executes the program stored in the storage unit 11, the standard-body imaging condition modification unit 12 and the modification unit 13 may be realized by a microcomputer or a specialized circuit, for example.

The computer 10 receives a configuration of the x-ray system (Step S11). The configuration of the x-ray system refers to the presence or the absence of the anti-scatter device 70, the type of the anti-scatter device 70, and the value of the distance b, for example.

The computer 10 receives the type of the examined body part to be imaged by the image-capturing person (for instance, the chest or the abdomen: more specifically, the lung fields or the mediastinum in the case of the chest, for example) (Step S12). Specifically, the computer 10 receives the type of the examined body part entered into the operation panel 20 by the image-capturing person.

Next, the standard-body imaging condition modification unit 12 modifies a standard-body imaging condition to a first imaging condition, using a converted value obtained by converting the examinee's body thickness into a phantom thickness by taking the examinee's body build into consideration (Step S13). Here, the standard-body imaging condition is a predetermined imaging condition under which an x-ray image, of the standard body, having an appropriate radiographic effect is obtained. The first imaging condition is an imaging condition for the examinee's body (the examined body part), and is an imaging condition under which an x-ray image having a radiographic effect equivalent to the radiographic effect of the x-ray image obtained under the standard-body imaging condition is obtained. The predetermined standard-body imaging condition is, for example, an imaging condition stored in the storage unit 11 in advance, and is an imaging condition under which an x-ray image, of the standard body, having an appropriate radiographic effect is obtained (here, the standard body refers to the standard body for each size of small, medium, and large when, as the examined body part, the lung fields of the chest are classified into small, medium, and large by size, for example). For example, the standard-body imaging condition includes: a tube voltage which takes a radiographic contrast for the standard body into consideration; an optimal mAs value based on the granularity (radiographic mottle) attributable to the quantity of photons incident on the x-ray image; and an optimal SID based on the anamorphosis of the x-ray image and a request for a real size image. Then, using the converted value obtained by converting the examinee's body thickness into a phantom thickness by taking the examinee's body build into consideration, the standard-body imaging condition modification unit 12 modifies, through high-speed computation, the standard-body imaging condition to the first imaging condition under which an appropriate image (an x-ray image having a radiographic effect equivalent to the radiographic effect of the x-ray image obtained under the standard-body imaging condition) is obtained. It should be noted that the phantom is, for example, a water phantom; however, it is also possible to use milk, salt water, or acrylic, for example, instead of water. The operations in Step S13 (operations of the standard-body imaging condition modification unit 12) will be described in detail with reference to FIG. 4.

Figure 4:
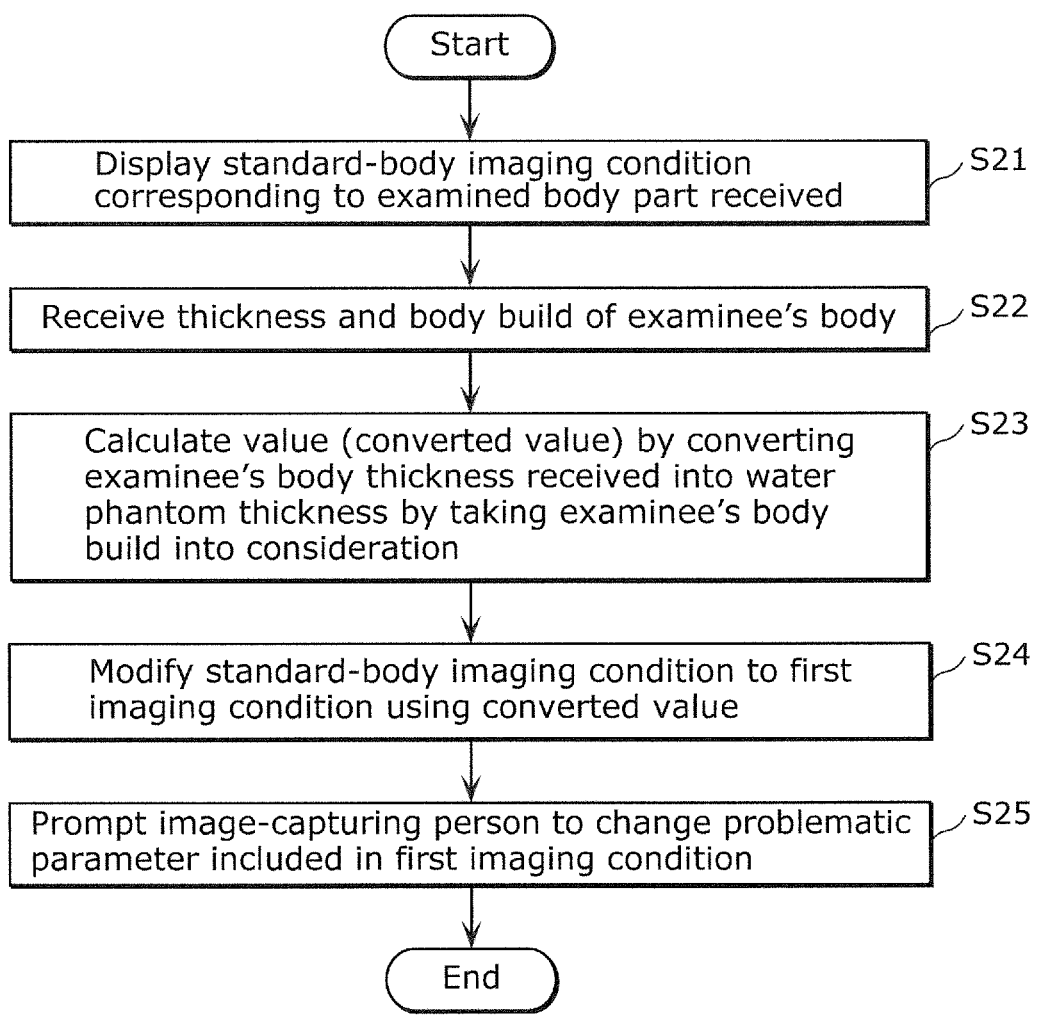
FIG. 4 is a flow chart illustrating an example of operations of a standard-body imaging condition modification unit according to an embodiment.

FIG. 4 is a flow chart illustrating an example of operations of the standard-body imaging condition modification unit 12 according to an embodiment.

The standard-body imaging condition modification unit 12 displays, on the display unit, the standard-body imaging condition corresponding to the examined body part received by the computer 10 (Step S21). With this, the image-capturing person can recognize the standard-body imaging condition for the standard body.

Next, the standard-body imaging condition modification unit 12 receives the thickness (for example, the thickness from the chest to the back) and the body build (for example, muscular, standard, or fatty) of the examinee's body (Step S22). Specifically, the computer 10 receives the thickness and the body build of the examinee's body entered into the operation panel 20 by the image-capturing person.

Next, the standard-body imaging condition modification unit 12 calculates a converted value by converting the received examinee's body thickness into a phantom thickness by taking the received examinee's body build into consideration (Step S23). The details of the processing in Step S23 will be described below.

Equation 1 represents the relationship between the radiographic effect and exp(-ud) that is a change in the x-rays attenuated by the examinee's body. Each of $V^n$, s, f, B, and G in Equation 1 can be easily calculated, and are thus replaced with a constant J. Furthermore, Z can be included in the constant J because Z is a fixed value for each x-ray tube used. The product of i and t is treated as the mAs value and is expressed as q (mAs value). Thus, Equation 1 can be rewritten as the following Equation 4.

[Math. 4]

$$E = WJ \frac{q}{r^2} e^{-ud} \quad \text{(Equation 4)}$$

Furthermore, Equation 4 can be rewritten as the following Equation 5.

[Math. 5]

$$ln(q) = ud + ln(E) - ln(WJ) + 2ln(r) \quad \text{(Equation 5)}$$

Moreover, with the radiographic effect E being fixed, Equation 5 can be rewritten as the following Equation 6 by collectively replacing ln(E)−ln(WJ) with a constant L.

[Math. 6]

$$ln(q) = ud + L + 2ln(r) \quad \text{(Equation 6)}$$

r is the SID and can be easily calculated, and thus L+2ln(r) can be set as a constant. Accordingly, Equation 6 can be seen as a linear equation having the examinee's body thickness d (cm) as a variable. Then, assuming the phantom as the examined body part to be imaged, u and L can be calculated by obtaining, through an experiment for each configuration of the x-ray system, the value of ln(q) with which an appropriate image can be obtained, by using two phantoms having different thicknesses. However, since the phantom and the examinee's body are different in density, it is necessary to convert the examinee's body thickness d (cm) into the phantom thickness α (cm) by taking the examinee's body build into consideration.

For example, when the x-ray system has a particular configuration (for example, when the anti-scatter device 70 is a standing anti-scatter device), and the imaging condition for the chest of the standard body includes, for example, a tube voltage of 120 kVp and an SID of 200 cm, it can be understood through an experiment that a mAs value q of 4.3 mAs is necessary for obtaining an appropriate image of a 10-cm-thick phantom. Similarly, it can be understood through an experiment that a mAs value q of 21.5 mAs is necessary for obtaining an appropriate image of a 20-cm-thick phantom. u is calculated as 0.161 and L is calculated as −10.747 by solving simultaneous equations obtained by substituting, into Equation 6, the value obtained through an experiment using the 10-cm-thick phantom and the value obtained through an experiment using the 20-cm-thick phantom. Accordingly, Equation 6 can be rewritten as the following Equation 7.

[Math. 7]

$$ln(q) = 0.161\alpha - 10.747 + 2ln(200) \quad \text{(Equation 7)}$$

Summarizing Equation 7 gives the following Equation 8.

[Math. 8]

$$ln(q) = 0.161\alpha - 0.151 \quad \text{(Equation 8)}$$

Next, the following is a description of an equation for converting the examinee's body thickness d in the case of imaging the lung fields of the chest into the phantom thickness α (a converted value) by taking the examinee's body build into consideration.

With the above particular configuration of the x-ray system, q is derived as 3.2 mAs and α is calculated as 8.162 cm from Equation 8 when the standard-body imaging condition for the chest of the standard body assuming a thickness of 20 cm and a standard body build includes a tube voltage of 120 kVp, a tube current of 100 mA, an imaging time of 0.032 s, and an SID of 200 cm.

With this, when the examined body part is the lung fields of the chest, for example, the following Equation 9 can be written as a relational expression between α and d.

[Math. 9]

$$\alpha = \frac{d}{2} - 1.838 + nk1 \quad \text{(Equation 9)}$$

Here, nk1 is a value indicating the influence of the body build when the examined body part is the lung fields of the chest. For example, nk1 is −4 for a thin body build, −2 for a fatty body build, 0 for a standard body build, and 2 for a muscular body build. When capturing an x-ray image, the image-capturing person determines the examinee's body thickness and determines the type of the examinee's body build from among the types mentioned above, and enters the determined information into the computer 10 (the operation panel 20) as described in regard to Step S22.

For example, when the examinee's body 100 the chest lung fields of which are to be imaged has a thickness of 21 cm and a muscular body build, and when the converted value is α1, α1 is calculated from Equation 9 using the computer 10 as shown in Equation 10.

[Math. 10]

$$\alpha1 = 21/2 - 1.838 + 2 \quad \text{(Equation 10)}$$

Thus, the converted value α1 obtained by converting the thickness (21 cm) of the examinee's body 100 into a phantom thickness by taking the body build (muscular body build) of the examinee's body 100 into consideration is calculated as 10.662 cm. In the manner as described, the processing in Step S22 is performed.

It should be noted that Equation 6 can be rewritten as the following Equation 11 when: the x-ray system includes a lying anti-scatter device as the anti-scatter device 70; the SID is 115 cm; and a 10-cm-thick phantom and a 20-cm-thick phantom are used.

[Math. 11]

$$\ln(q) = 0.116\alpha - 0.447 \quad \text{(Equation 11)}$$

Furthermore, Equation 6 can be rewritten as the following Equation 12 when: the x-ray system does not include the anti-scatter device 70; the SID is 100 cm; and a 10-cm-thick phantom and a 20-cm-thick phantom are used.

[Math. 12]

$$\ln(q) = 0.198\alpha \quad \text{(Equation 12)}$$

Moreover, the relational expression between α and d can be written as the following Equation 13 when the examined body part is the abdomen.

[Math. 13]

$$\alpha = d - 2 + nk2 \quad \text{(Equation 13)}$$

Here, nk2 is a value indicating the influence of the body build when the examined body part is the abdomen. For example, nk2 is −1 for a thin body build, −1.5 for a fatty body build, 1.5 for a standard body build, and 3.5 for a muscular body build.

Moreover, the relational expression between α and d can be written as the following Equation 14 when the examined body part is a limb.

[Math. 14]

$$\alpha = d + nk3 \quad \text{(Equation 14)}$$

Here, nk3 is a value indicating the influence of the body build when the examined body part is a limb. For example, nk3 is −d×0.2 for a thin body build, −d×0.1 for a fatty body build, 0 for a standard body build, and d×0.2 for a muscular body build.

Then, the standard-body imaging condition modification unit 12 modifies the standard-body imaging condition to the first imaging condition using the converted value calculated (Step S24).

When the mAs value used when capturing an image of the examinee's body 100 having a muscular body build and a thickness of 21 cm is q1, ln(q1) is calculated as 1.566 from Equation 8, and q1 is thereby derived as 4.785. For example, when the tube current is the same as that for the standard body, the tube current is 100 mA, and thus the imaging time is 0.04785 s. That is to say, the first imaging condition for obtaining an appropriate image with the above particular configuration of the x-ray system in the case of capturing an x-ray image of the examinee's body 100 includes a tube voltage of 120 kVp, a tube current of 100 mA, an imaging time of 0.04785 s, and an SID of 200 cm. In such a manner, the standard-body imaging condition modification unit 12 modifies the standard-body imaging condition for the standard body having a standard body build and a thickness of 20 cm to the first imaging condition for the examinee's body 100 having a muscular body build. However, the image capturing is not possible in some cases when the imaging time is 0.04785 s, depending on the x-ray system. For example, when the x-ray system is a system the imaging time for which is changeable at 0.05-s intervals, the standard-body imaging condition modification unit 12 displays, on the display unit, 0.04785 s as the optimal imaging time, for example, and also displays, on the display unit, as candidates for the imaging time to which the imaging time included in the standard-body imaging condition can be changed, 0.045 s and 0.050 s that are parameters closest to 0.04785 s. By doing so, the standard-body imaging condition modification unit 12 prompts the image-capturing person to select an imaging time from these candidates displayed.

It should be noted that the storage unit 11 stores in advance: the standard-body imaging condition for the standard body; the relational expression between the mAs value and the converted value such as Equation 8, Equation 11, or Equation 12; and a converting equation such as Equation 9, Equation 13, or Equation 14, for each configuration of the x-ray system and for each examined body part. The storage unit 11 also stores in advance limits such as a usable tube voltage range, a minimum usable mAs value, and a usable SID range from the standpoint of the configuration of the x-ray system. In addition, the storage unit 11 stores in advance, as one of the limits, a longest imaging time corresponding to the examined body part.

Next, when the parameters included in the first imaging condition include a problematic parameter, the standard-body imaging condition modification unit 12 prompts the image-capturing person to change the problematic parameter (Step S25). For example, the standard-body imaging condition modification unit 12 shows (displays on the display unit, for example) that the problematic parameter should be changed. The problematic parameter refers to, for example, a parameter that falls outside the limits stored in the storage unit 11. The modification unit 13, which will be described later, changes the value of at least one of the parameters included in the first imaging condition to an arbitrary value. Accordingly, the standard-body imaging condition modification unit 12 prompts the image-capturing person to cause the modification unit 13 to: set the problematic parameter as the parameter whose value is to be changed to the arbitrary value; and set, as the arbitrary value, a value within the limits stored in the storage unit 11.

For example, when the examined body part to be imaged is the chest, and the imaging time included in the first imaging condition exceeds an imaging time predetermined for controlling blur caused by cardiac motion, the standard-body imaging condition modification unit 12 prompts the image-capturing person to cause the modification unit 13 to: set at least one parameter to the imaging time; and set, as the arbitrary value, a value not exceeding the predetermined imaging time.

Further, for example, when the examined body part to be imaged is the abdomen, and the imaging time included in the first imaging condition exceeds an imaging time predetermined for controlling blur caused by peristalsis motion of gastrointestine, the standard-body imaging condition modification unit 12 prompts the image-capturing person to cause the modification unit 13 to: set at least one parameter to the imaging time; and set, as the arbitrary value, a value not exceeding the predetermined imaging time.

Furthermore, for example, when the mAs value included in the first imaging condition is less than the mAs value predetermined for each examined body part to be imaged and for each converted value according to the performance of the x-ray system based on the radiographic mottle, the standard-body imaging condition modification unit 12 prompts the image-capturing person to cause the modification unit 13 to: set at least one parameter to the mAs value; and set, as the arbitrary value, a value exceeding the predetermined mAs value.

Specifically, the standard-body imaging condition modification unit 12 determines whether or not the mAs value included in the first imaging condition is appropriate, according to: the mAs value (product of tube current (mA) and imaging time (second)) that is based on the radiographic mottle; and the minimum mAs value stored in the storage unit 11. More specifically, from the standpoint of the radiographic mottle, the granularity of the x-ray image deteriorates when, for example, the mAs value is small, due to a small quantity of photons generated. For this reason, the minimum mAs value is determined according to the thickness of the examinee's body (examined body part) to be imaged and the performance of the components included in the x-ray system. Accordingly, the storage unit 11 stores in advance a minimum mAs value corresponding to the performance of the components included in the x-ray system, for example. For example, the storage unit 11 stores in advance the minimum mAs value according to a restriction such as "the mAs value needs to be 1.5 or greater when imaging the lung fields of the chest and using the anti-scatter device". The standard-body imaging condition modification unit 12 then determines whether or not the mAs value included in the first imaging condition is less than the minimum mAs value, and when the mAs value included in the first imaging condition is less than the minimum mAs value, prompts the image-capturing person to change (increase) the mAs value included in the first imaging condition.

Furthermore, for example, when the examined body part is a part, such as the lung fields of the chest or the abdomen, involving motion (for example, cardiac motion or peristalsis motion of gastrointestine), the storage unit 11 stores in advance the longest imaging time corresponding to the examined body part, to control blur in the x-ray image. Thus, for example, the standard-body imaging condition modification unit 12 determines, based on the longest imaging time stored in the storage unit 11, whether or not the imaging time included in the first imaging condition is appropriate. Specifically, the standard-body imaging condition modification unit 12 determines whether or not the imaging time included in the first imaging condition is greater than the longest imaging time, and when the imaging time included in the first imaging condition is greater than the longest imaging time, prompts the image-capturing person to change (reduce) the imaging time included in the first imaging condition.

In the manner as described, the standard-body imaging condition modification unit 12 calculates a parameter of the first imaging condition (such as the mAs value or the imaging time) through high-speed computation, using, for example: the standard-body imaging condition for the standard body and Equations 7 and 9 stored in the storage unit 11 in advance; and the thickness and the body build of the examinee's body entered by the image-capturing person, and displays the resulting first imaging condition on the display unit. In addition, when a problematic parameter is included in the parameters of the first imaging condition, the standard-body imaging condition modification unit 12 displays on the display unit that the problematic parameter should be changed.

In general, an image-capturing person who is not used to the x-ray imaging performs x-ray imaging using the first imaging condition, whereas an experienced image-capturing person attempts to change a parameter included in the first imaging condition because the experienced image-capturing person takes motion of the examined body part and the magnification ratio into consideration. For example, the image-capturing person attempts to reduce the imaging time when he/she considers that blur has occurred/will occur in the x-ray image due to the motion of the examined body part, and attempts to reduce the tube current by using an x-ray tube having a small focal spot when he/she considers that, with the current magnification ratio, blur occurs due to the x-ray tube focal spot. It is, however, necessary to change the parameters included in the first imaging condition to achieve a radiographic effect equivalent to the radiographic effect achieved under the first imaging condition.

Moreover, as described earlier, since the standard-body imaging condition modification unit 12 prompts the image-capturing person to change (increase or reduce) the value of the problematic parameter when the problematic parameter is included in the parameters of the first imaging condition, the image-capturing person attempts to change the value of a parameter included in the first imaging condition.

When the image-capturing person (i) determines, from the standpoint of motion of the examined body part and the magnification ratio, for example, that the first imaging condition obtained by the modification performed by the standard-body imaging condition modification unit 12 needs further modification in order to achieve a radiographic effect equivalent to the radiographic effect achieved under the first imaging condition, and (ii) changes the value of at least one of the parameters included in the first imaging condition to an arbitrary value, the modification unit 13 identifies the remaining unchanged parameters based on the changed parameter. For example, the modification unit 13 displays parameter cells on the display unit, and identifies, among the parameter cells, parameters unoperated by the image-capturing person (for example, parameters whose cells are left blank) as the remaining unchanged parameters.

It should be noted that in general, an image projected onto the x-ray detector system becomes more visible when enlarged geometrically. On the other hand, the image may be more sharp and visible when not enlarged, depending on the degree of blur caused by the area of the x-ray tube focal spot or blur caused by motion of the examined body part. In other words, an optimal magnification ratio depends on the degree of blur. Taking into consideration motion of the examined body part and the magnification ratio refers to taking into consideration an optimal magnification ratio and the degree of sharpness. It should be noted that the magnification ratio, denoted as M, is represented by the following Equation 15.

[Math. 15]

$$M = \frac{b}{a} \quad \text{(Equation 15)}$$

a represents the distance between the x-ray tube focal spot and the examined body part plane (SOD), and b represents the distance between the x-ray tube focal spot and the x-ray detector system plane (SID).

In view of this, the modification unit 13 modifies the first imaging condition to the second imaging condition under which an x-ray image having a radiographic effect equivalent to the radiographic effect of the x-ray image obtained under the first imaging condition is obtained, by changing the value of at least one of the parameters included in the first imaging condition to an arbitrary value, and changing the values of the remaining parameters using the arbitrary value and an approximate function (Step S14). Specifically, the first imaging condition modified by the modification unit 13 to the second imaging condition is the condition obtained by the standard-body imaging condition modification unit 12 modifying the standard-body imaging condition. The operations in Step S14 (operations of the modification unit 13) will be described in detail with reference to FIG. 5 to FIG. 11.

Figure 5:
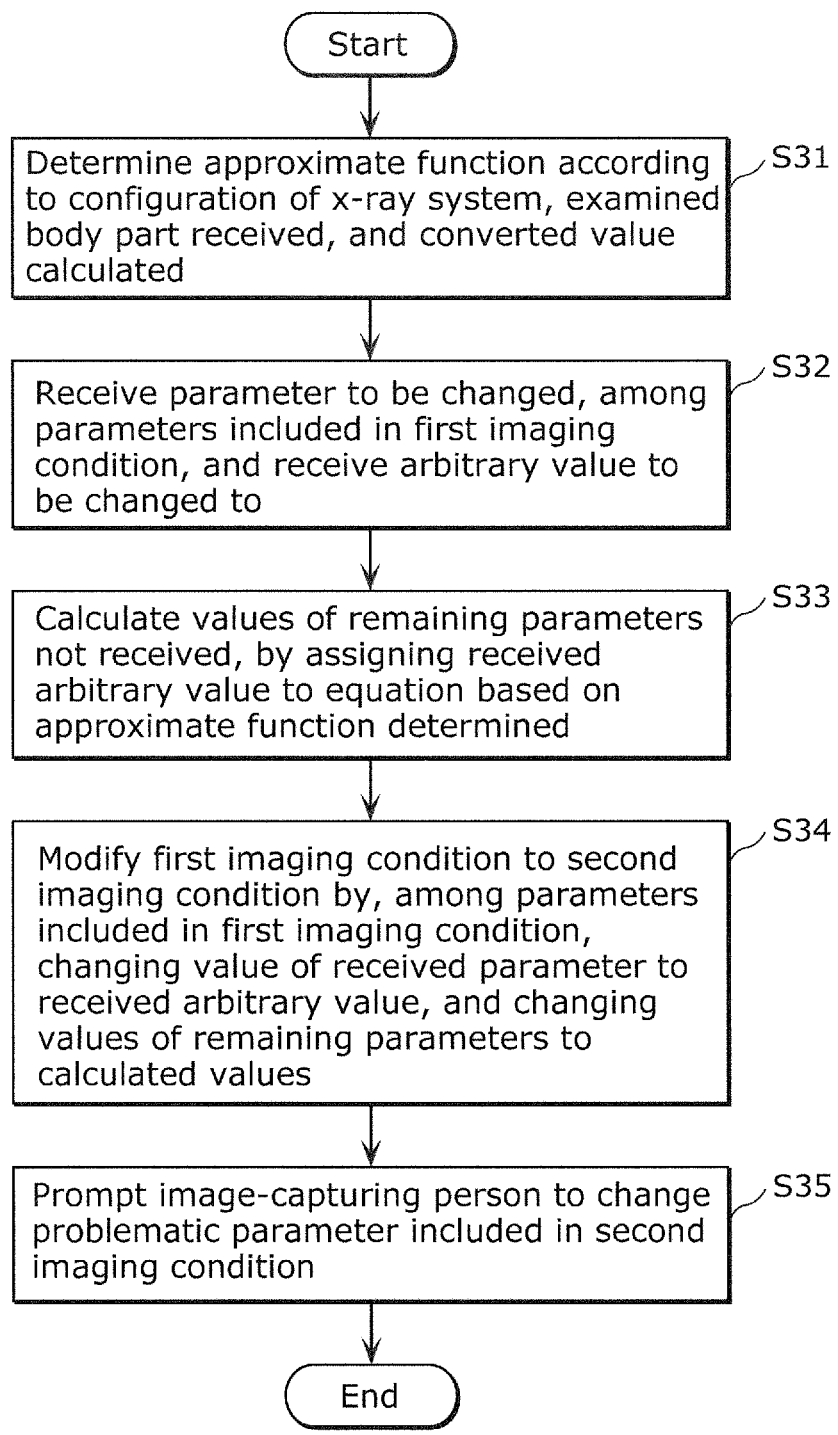
FIG. 5 is a flow chart illustrating an example of operations of a modification unit according to an embodiment.

FIG. 5 is a flow chart illustrating an example of operations of the modification unit 13 according to an embodiment.

First, the modification unit 13 determines an approximate function according to the configuration of the x-ray system, the type of the examined body part received by the computer 10, and the converted value calculated by the standard-body imaging condition modification unit 12 (Step S31).

Here, the conventional exponential method will be described prior to describing the approximate function according to the present disclosure.

Figure 6:
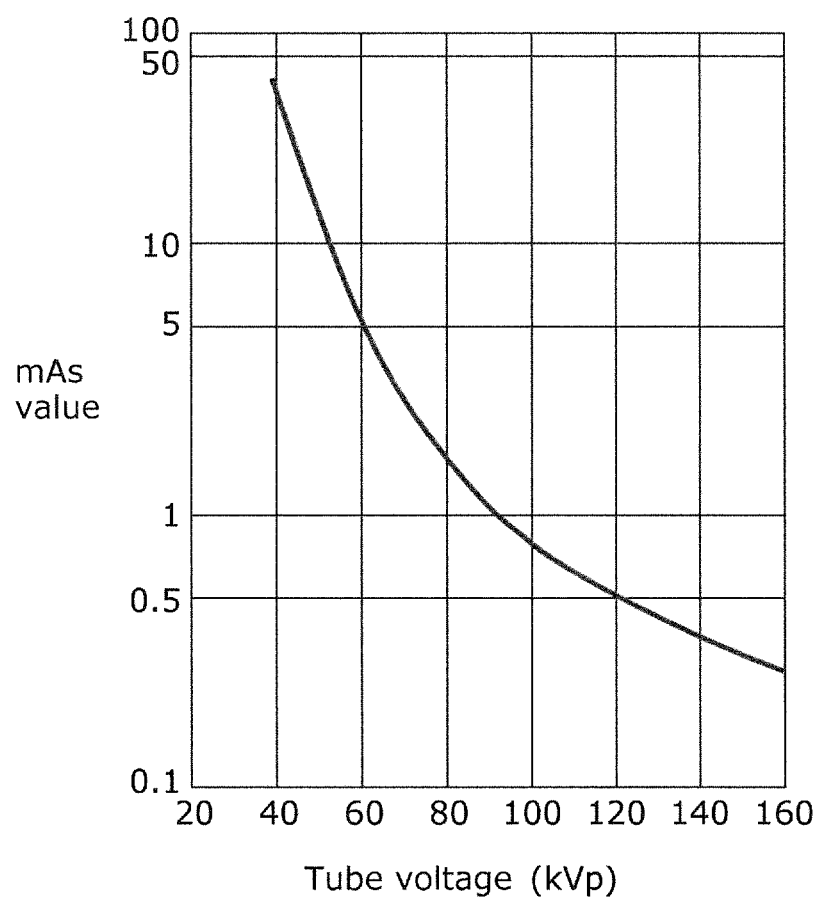
FIG. 6 is a diagram illustrating an example of a conventional isodensity curve.

With the conventional exponential method, an isodensity curve is created as illustrated in FIG. 6, for example.

FIG. 6 is a diagram illustrating an example of a conventional isodensity curve. The isodensity curve is a curve showing a relationship between the tube voltage and the mAs value (the product of tube current (mA) and imaging time (second)) when the same radiographic effect can be achieved. In FIG. 6, the horizontal axis shows the tube voltage, and the vertical axis shows the mAs value.

The isodensity curve illustrated in FIG. 6 is an example of curves created through an experiment for each configuration of the x-ray system and each examined body part (Note that the SID is constant). FIG. 6 shows, for example, that in the case where an appropriate image can be obtained at a tube voltage of 40 kVp and a mAs value of 40 mAs, and when the tube voltage is changed to a new tube voltage of 60 kVp, it is possible to obtain an x-ray image having a radiographic effect equivalent to the radiographic effect of the appropriate image obtained at the tube voltage of 40 kVp and the mAs value of 40 mAs, if the mAs value is changed to a new mAs value of 5 mAs.

Here, Equation 3 can be rewritten as the following Equation 16.

[Math. 16]

$$\frac{(V1)^{n1}}{(V2)^{n2}} = \frac{(i2)(t2)}{(r2)^2} \frac{(r1)^2}{(i1)(t1)} \quad \text{(Equation 16)}$$

Furthermore, with the conventional exponential method, the left-hand side of Equation 16 (a ratio of a term related to a tube voltage before change and a term related to a new tube voltage after change) is treated as a tube voltage coefficient P. The tube voltage coefficient P is represented by the exponential function shown in the following Equation 17.

[Math. 17]

$$P = \frac{(V1)^{n1}}{(V2)^{n2}} \quad \text{(Equation 17)}$$

It should be noted that when the SID is constant, the tube voltage coefficient P means a ratio of a new mAs value after change and a mAs value before change as shown by the right-hand side of Equation 16. In other words, once the tube voltage coefficient P is calculated from Equation 17, the new mAs value after change can be calculated from the calculated tube voltage coefficient P and the mAs value before change.

With the conventional exponential method, n1 and n2 are not strictly determined. For example, when assuming n1≈n2, and n1 and n2, which are exponentials, are replaced with n, the following Equation 18 can be obtained from Equation 3 if the same SID is used.

[Math. 18]

$$40^n \times 40 = 60^n \times 5 \quad \text{(Equation 18)}$$

Therefore, it is calculated that n≈5.1.

Using Equation 17, the tube voltage coefficient P can be represented by the following Equation 19.

[Math. 19]

$$P = \frac{(V1)^{n1}}{(V2)^{n2}} = \frac{40^{5.1}}{60^{5.1}} = 0.13 \quad \text{(Equation 19)}$$

With the conventional exponential method, n may be equal to 4 at a rough estimate when the tube voltage before change is in a range from 40 kVp to 100 kVp, for example. For example, when the tube voltage before change is 40 kVp and the new tube voltage after change is 60 kVp, the tube voltage coefficient P can be represented by the following Equation 20.

[Math. 20]

$$P = \frac{(V1)^{n1}}{(V2)^{n2}} = \frac{40^4}{60^4} = 0.198 \quad \text{(Equation 20)}$$

Furthermore, n may be equal to 3 at a rough estimate when the tube voltage before change is in a range from 110 kVp to 150 kVp. For example, when the tube voltage before change is 110 kVp and the new tube voltage after change is 120 kVp, the tube voltage coefficient P can be represented by the following Equation 21.

[Math. 21]

$$P = \frac{(V1)^{n1}}{(V2)^{n2}} = \frac{110^3}{120^3} = 0.606 \qquad \text{(Equation 21)}$$

Figure 7:
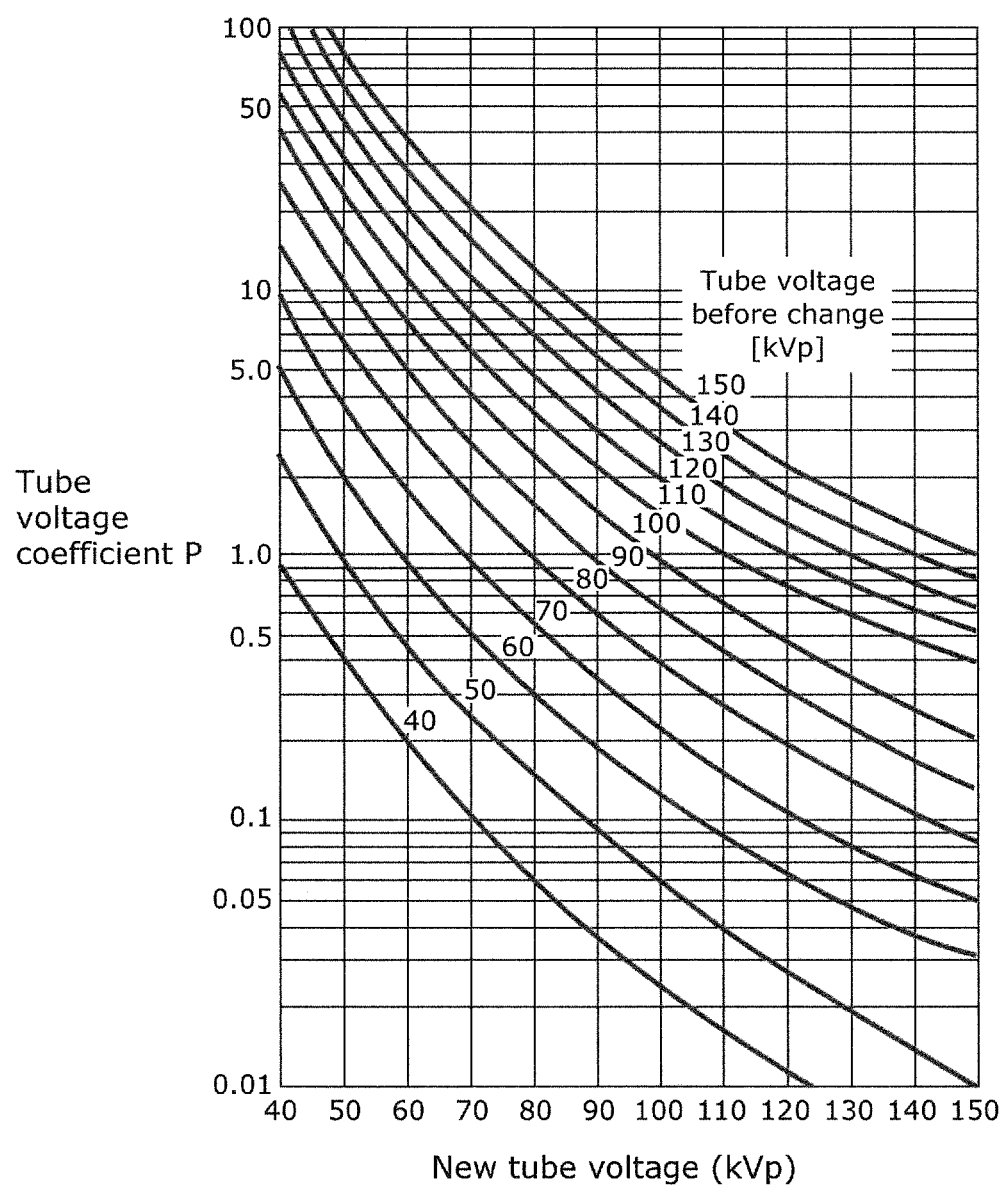
FIG. 7 is a diagram illustrating an example of a conventional tube voltage coefficient graph.

A graph obtained by plotting the relationship between the tube voltage coefficient P and the new tube voltage V2 obtained in the above manner is the tube voltage coefficient graph illustrated in FIG. 7.

FIG. 7 is a diagram illustrating an example of a conventional tube voltage coefficient graph. In FIG. 7, the vertical axis shows the tube voltage coefficient P, and the horizontal axis shows the new tube voltage V2. For example, when the tube voltage of 60 kVp is to be changed to a new tube voltage of 40 kVp, the curve having the tube voltage of 60 kVp before change shows that the tube voltage coefficient P corresponding to the new tube voltage of 40 kVp is approximately 5.0. This therefore indicates that it is only necessary to multiply the mAs value included in the imaging condition applied when the tube voltage before change is 60 kVp, by approximately 5. Furthermore, when an appropriate image is obtained at the tube voltage of 80 kVp before change and the image-capturing person wishes to multiply the mAs value of this case by 0.4, the curve having the tube voltage of 80 kVp before change shows that the new tube voltage when the tube voltage coefficient P is 0.4 is approximately 100 kVp. In such a manner as described, with the conventional exponential method, a curve showing the relationship between the tube voltage coefficient P and the new tube voltage V2 is created by calculating the n value at a rough estimate and treating the left-hand side of Equation 16 as the tube voltage coefficient P. By doing so, the new tube voltage and the new mAs value after change can be read from the curve.

With the conventional exponential method, n1 is treated almost equal to n2 or a rough value is assigned to the n value for convenience as described earlier. Such a rough estimation does not cause a significant error when the tube voltage coefficient P is in a range from 0.5 to 2.0, for example. The conventional exponential method, however, is impractical because it causes an error to increase exponentially when the tube voltage coefficient P is less than 0.5 or greater than 2.0, for example.

In contrast, the present disclosure treats the right-hand side of Equation 16 as a mAs value coefficient Q. The mAs value coefficient Q can be represented by the following Equation 22.

[Math. 22]

$$Q = \frac{(i2)(t2)}{(r2)^2} \frac{(r1)^2}{(i1)(t1)} \qquad \text{(Equation 22)}$$

The present disclosure uses an approximate function that is for approximating to the relationship between the mAs value coefficient Q and the new tube voltage V2 and that does not have n (a power peculiar to the tube voltage) as the exponential as shown in Equation 22. The approximate function is for approximating to a curve obtained by plotting, for each of a plurality of imaging conditions, a relationship between a new tube voltage included in each of the plurality of imaging conditions and a mAs value coefficient Q represented by Equation 22, where i2, t2, and r2 represent a new tube current, an imaging time after change (a new imaging time), and an imaging distance after change (a new imaging distance), respectively, which are included in the plurality of imaging conditions, and i1, t1, and r1 represent the tube current, the imaging time, and the imaging distance, respectively, which are included in an imaging condition before change (a first imaging condition), the plurality of imaging conditions being determined through an experiment so as to obtain an x-ray image having a radiographic effect equivalent to the radiographic effect of an x-ray image obtained under the imaging condition before change (the first imaging condition). The plurality of imaging conditions under which an x-ray image having a radiographic effect equivalent to a radiographic effect of an x-ray image obtained under the first imaging condition is obtained are imaging conditions obtained by actual measurement performed for each configuration of the x-ray system, each examined body part, and each converted value. By plotting the value of the mAs value coefficient Q calculated by assigning the first imaging condition and each of the plurality of actually-measured imaging conditions to Equation 22, a curve having the mAs value coefficient Q on the vertical axis and the new tube voltage V2 on the horizontal axis is created. To approximate this curve, an approximate function having the new tube voltage as a variable is created.

It should be noted that the mAs value coefficient Q in Equation 22 is a coefficient obtained by normalizing a new mAs value per unit surface area used when generating x-rays emitted from a given center, using a mAs value per unit surface area used when generating x-rays emitted from a given center in the first imaging condition.

When the approximate function for approximating to the curve is represented by Y(V2), Y(V2) can be calculated by the following Equation 23.

[Math. 23]

$$Y(V2) = \frac{(i2)(t2)}{(r2)^2} \frac{(r1)^2}{(i1)(t1)} = \frac{\frac{q2}{(r2)^2}}{\frac{q1}{(r1)^2}} \qquad \text{(Equation 23)}$$

It should be noted that q2 equals i2×t2, q1 equals i1×t1, and V2 is a new tube voltage.

As described above, the conventional exponential method uses an equation including n (a power peculiar to the tube voltage) as the exponential as shown in Equation 17. In contrast, the present disclosure uses an equation that does not include n (a power peculiar to the tube voltage) as the exponential as shown in Equation 22.

Figure 8:
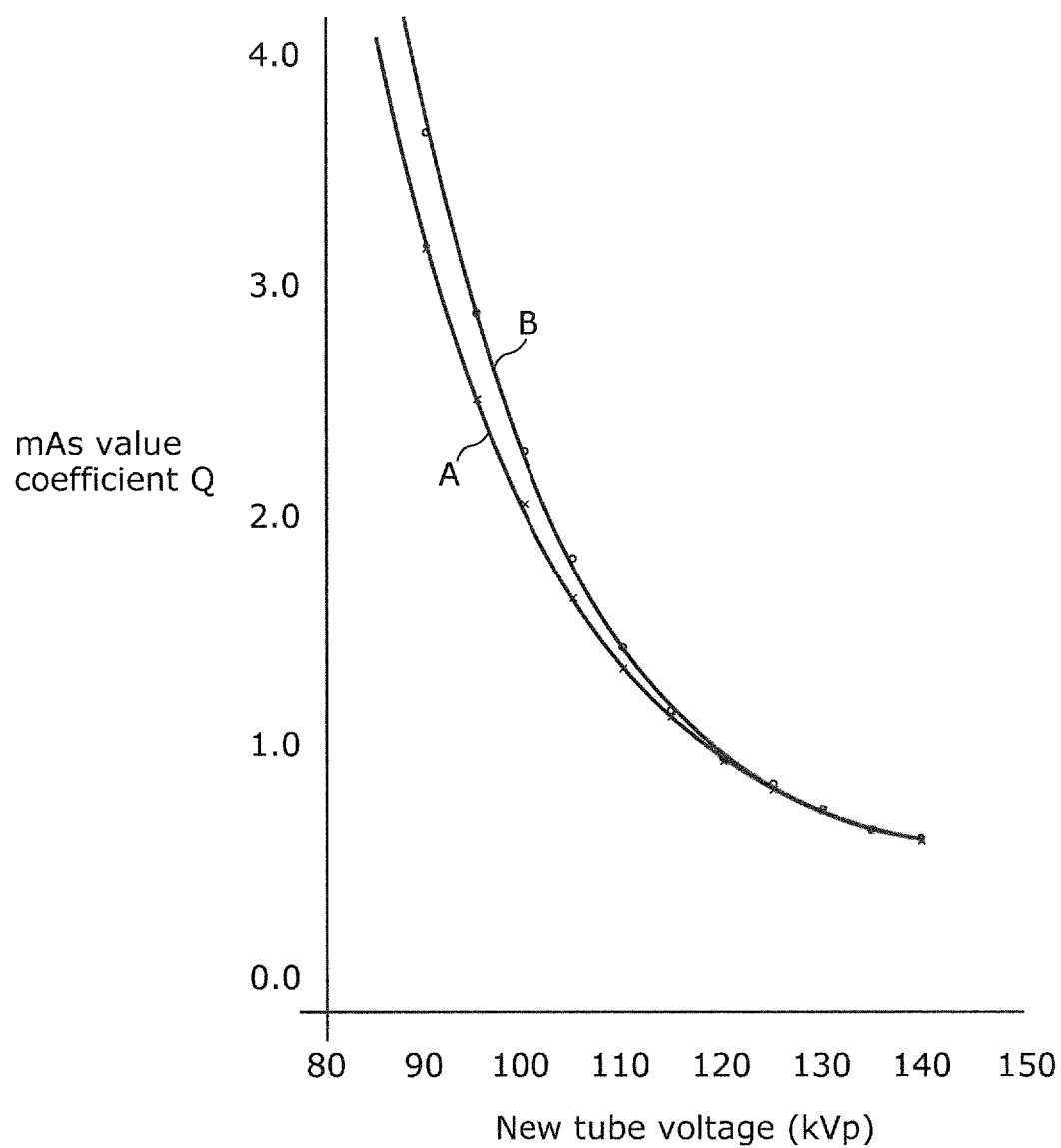
FIG. 8 is a diagram illustrating examples of a curve showing a relationship between mAs value coefficient and new tube voltage.

The following describes, with reference to FIG. 8 and FIG. 9, (i) a curve showing a relationship between the mAs value coefficient Q and the new tube voltage V2 and (ii) the approximate function Y(V2) for approximating to the curve.

FIG. 8 is a diagram illustrating examples of a curve showing a relationship between the mAs value coefficient Q and the new tube voltage V2. For example, assuming the case of imaging the lung fields of the chest, the first imaging condition, when likening a 10-cm-thick phantom to the examinee's body, includes a tube voltage of 120 kVp, a tube current of 100 mA, an imaging time of 0.043 s, and an SID of 200 cm. Then, the mAs values are obtained through an experiment while changing the tube voltage with the SID kept constant, for example, so as to obtain an x-ray image having a radiographic effect equivalent to the radiographic effect of the x-ray image obtained under the first imaging condition. Assuming, in Equation 22: r1=r2=200 cm; i1=100 mA; t1=0.043 s; and i2×t2 being solved as the mAs values obtained through an experiment, the value of the mAs value coefficient Q is calculated for each new tube voltage changed when obtaining the mAs value. The curve denoted as A in FIG. 8 is obtained by plotting the relationship between the mAs value coefficient Q and the new tube voltage V2 under the above condition. It should be noted that since the SID is kept constant, the mAs value coefficient Q shown in FIG. 8 is a value obtained by dividing the mAs values obtained through an experiment by the mAs value in the first imaging condition. Furthermore, while the following description focuses on the curve denoted as A in FIG. 8, the curve denoted as B in FIG. 8 is a curve obtained by plotting the relationship between the mAs value coefficient Q and the new tube voltage V2 when likening a 20-cm-thick phantom to the examinee's body.

As described earlier, the tube current is 100 mA and the imaging time is 0.043 s in the first imaging condition, and thus the denominator for the mAs value coefficient Q is 4.3 mAs. The curve denoted as A in FIG. 8 shows that: it is only necessary to set the new tube voltage to approximately 130 kVp when the image-capturing person wishes to multiply the mAs value in the first imaging condition by 0.8; and it is only necessary to set the new tube voltage to approximately 101 kVp when the image-capturing person wishes to multiply the mAs value in the first imaging condition by 2.

However, a feature of the present disclosure lies in modifying the first imaging condition to the second imaging condition through high-speed computation using a computer. Thus, an approximate function Y(V2) for approximating to the curve is used. It is, however, very difficult to approximate to the curve using a single approximate function, and thus approximate functions Y(V2) each of which accurately approximates to the curve in part are used.

Specifically, in the case of V2≤V1 or Q≥1, the following equation is used as the approximate function Y(V2).

[Math. 24]

$$Q = Y(V2) = \frac{\exp(k2)}{(V2)^{k1}} \quad \text{(Equation 24)}$$

Here, k1 and k2 represent values included in the approximate function for approximating to the curve showing the relationship between the mAs value coefficient Q and the new tube voltage V2, and are values corresponding to the phantom thickness. V2 represents a new tube voltage of the second imaging condition obtained by changing the tube voltage V1 of the first imaging condition.

In the case of V2>V1 or Q<1, the following equation is used as the approximate function Y(V2).
[Math. 25]

$$Q = Y(V2) = \exp(-(V2)^{k3} + k4) + k5 \quad \text{(Equation 25)}$$

Here, k3, k4, and k5 represent values included in the approximate function for approximating to the curve showing the relationship between the mAs value coefficient Q and the new tube voltage V2, and are values corresponding to the phantom thickness.

A database indicating the values of k1, k2, k3, k4, and k5 is prepared in advance so that Equation 24 and Equation 25 approximate to the curve that is actually measured for each converted value.

FIG. 9 is an example of a database which is prepared in advance for each configuration of the x-ray system and for each examined body part, and which associates the converted value with k1 to k5 included in the approximate function.

For example, when the examined body part 200 is the lung fields of the chest, a tube voltage of 120 kVp is generally adopted as the imaging condition. Thus, the tube voltage V1 included in the first imaging condition is set to 120 kVp. When the new tube voltage V2 is 120 kVp or less and the mAs value coefficient Q is 1 or greater, Equation 24 is used as the approximate function Y(V2).

When the new tube voltage V2 is greater than 120 kVp and the mAs value coefficient Q is less than 1, Equation 25 is used as the approximate function Y(V2).

In the case of the above-described examinee's body 100 having a thickness of 21 cm and a muscular body build, the converted value α1 is 10.662 cm. Thus, for example, the modification unit 13 determines, with reference to FIG. 9, an approximate function using k1 to k5 corresponding to the converted value 11 cm that is close to 10.662 cm. Accordingly, 3.95 as k1, 18.911 as k2, 0.538 as k3, 12.383 as k4, and 0.53 as k5 are assigned to Equation 24 and Equation 25, and thus, Equation 24 is rewritten as the following Equation 26, and Equation 25 is rewritten as the following Equation 27. Equation 26 and Equation 27 are for approximating to the curve showing the relationship between the mAs value coefficient Q and the new tube voltage V2.

[Math. 26]

$$Y(V2) = \frac{\exp(18.911)}{(V2)^{3.95}} \quad \text{(Equation 26)}$$

[Math. 27]

$$Y(V2) = \exp(-(V2)^{0.538} + 12.383) + 0.53 \quad \text{(Equation 27)}$$

Figure 10:
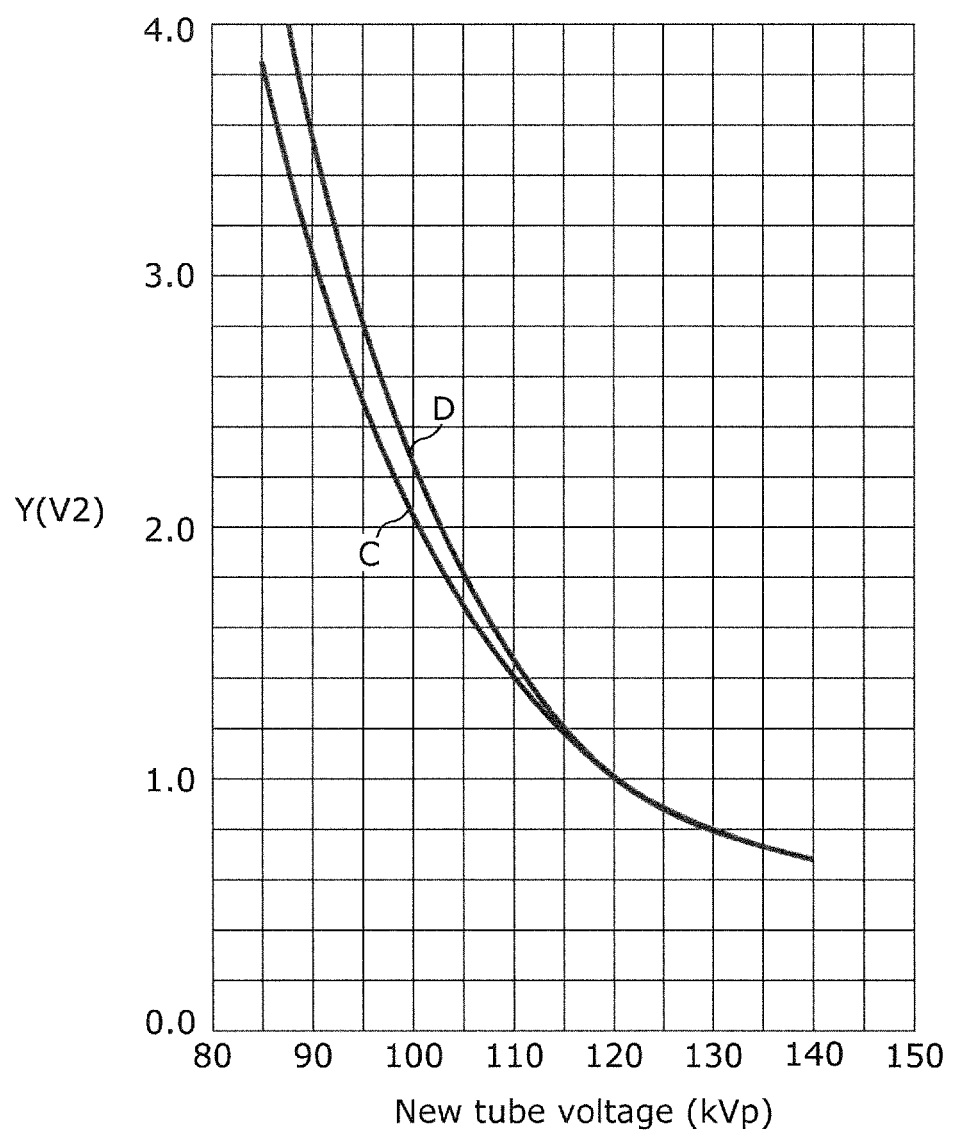
FIG. 10 is a diagram illustrating examples of approximate functions for approximating to the curves illustrated in FIG. 8.

FIG. 10 is a diagram illustrating examples of approximate functions for approximating to the curves illustrated in FIG. 8. It can be understood that the approximate function denoted as C in FIG. 10 is for approximating to the curve denoted as A in FIG. 8, whereas the approximate function denoted as D in FIG. 10 is for approximating to the curve denoted as B in FIG. 8.

The tube voltage coefficient graph has conventionally been used to obtain a new tube voltage which the tube voltage is to be changed to, despite the fact that the impact of scattering rays differs for each examinee's body depending on the performance of the components of the x-ray system and that the curves vary as with A and B illustrated in FIG. 8. In addition, the conventional method has been impractical because the tube voltage coefficient P includes an exponential function, thus causing an error to increase as described above.

In view of the above, the following are performed according to the present disclosure: converted values are calculated in advance by converting the thickness of the examinee's body into a phantom thickness by taking the body build of the examinee's body into consideration; an actually-measured curve showing a relationship between the mAs value coefficient Q and the new tube voltage V2 is created in advance for each configuration of the x-ray system used for obtaining an x-ray image, each examined body part to be imaged, and each converted value; and values of k1 to k5 are predetermined according to the configuration of the x-ray system, the examined body part, and the converted value so that Equation 24 and Equation 25 approximate to the curve, so as to prepare a database indicating the predetermined values of k1 to k5 as illustrated in FIG. 9.

In the manner as described, the modification unit 13 determines an approximate function according to the configuration of the x-ray system, the type of the examined body part, and the converted value.

Next, the modification unit 13 receives: at least one parameter to be changed, among the parameters included in the first imaging condition; and an arbitrary value to be changed to (Step S32).

Specifically, when the image-capturing person determines, from the standpoint of motion of the examined body part and the magnification ratio, that the first imaging condition obtained by the modification performed by the standard-body imaging condition modification unit 12 needs further modification in order to achieve a radiographic effect equivalent to the radiographic effect achieved under the first imaging condition, the image-capturing person enters, via the operation panel 20, for example, (i) at least one parameter to be changed, among the parameters included in the first imaging condition, and (ii) a value (an arbitrary value) which the value of the at least one parameter is to be changed to. For example, the modification unit 13 displays parameter cells on the display unit, and the image-capturing person enters the arbitrary value in a cell corresponding to the parameter to be changed. With this, with a change, to the arbitrary value, of the value of at least one parameter among the parameters included in the first imaging condition, the modification unit 13 identifies parameters corresponding to columns that are left blank, for example, as the remaining unchanged parameters.

Next, the modification unit 13 calculates the values of the remaining parameters that were not received in Step S32, by assigning the arbitrary value to the equation that is based on the approximate function determined (Step S33).

Equation 23, Equation 24, and Equation 25 can be rewritten as the equations shown in Equation 28 to Equation 37 below. It should be noted that Q=Y1 when Q≥1 or V2≤V1, and Q=Y2 when Q<1 or V2>V1. Equation 28, Equation 30, Equation 32, Equation 33, and Equation 34 are equations obtained when Q≥1 or V2≤V1, and Equation 29, Equation 31, Equation 35, Equation 36, and Equation 37 are equations obtained when Q<1 or V2>V1.

[Math. 28]

$$Y1 = \frac{\exp(k2)}{(V2)^{k1}} \quad \text{(Equation 28)}$$

[Math. 29]

$$Y2 = \exp(-(V2)^{k3} + k4) + k5 \quad \text{(Equation 29)}$$

[Math. 30]

$$V2 = \exp\left(\frac{k2 - \ln(Q)}{k1}\right) \quad \text{(Equation 30)}$$

[Math. 31]

$$V2 = \exp\left(\frac{\ln(k4 - \ln(Q - k5))}{k3}\right) \quad \text{(Equation 31)}$$

[Math. 32]

$$t2 = \frac{Y1 \times i1 \times t1 \times (r2)^2}{i2 \times (r1)^2} \quad \text{(Equation 32)}$$

-continued

[Math. 33]

$$r2 = \left|\sqrt{\frac{i2 \times t2 \times (r1)^2}{Y1 \times i1 \times t1}}\right| \quad \text{(Equation 33)}$$

[Math. 34]

$$i2 = \frac{Y1 \times i1 \times t1 \times (r2)^2}{t2 \times (r1)^2} \quad \text{(Equation 34)}$$

[Math. 35]

$$t2 = \frac{Y2 \times i1 \times t1 \times (r2)^2}{i2 \times (r1)^2} \quad \text{(Equation 35)}$$

[Math. 36]

$$r2 = \left|\sqrt{\frac{i2 \times t2 \times (r1)^2}{Y2 \times i1 \times t1}}\right| \quad \text{(Equation 36)}$$

[Math. 37]

$$i2 = \frac{Y2 \times i1 \times t1 \times (r2)^2}{t2 \times (r1)^2} \quad \text{(Equation 37)}$$

i1, t1, and r1 are known from the first imaging condition obtained by the modification performed by the standard-body imaging condition modification unit 12. Therefore, when parameters, such as i2, t2, and r2, among the parameters included in the second imaging condition are determined to be arbitrary values, it is possible to calculate V2 as the values of the remaining parameters of the second imaging condition through high-speed computation using a computer, by assigning the known values and the arbitrary values to Equation 23 and Equation 30 or 31. Similarly, when, for example, i2, t2, and V2 are determined to be arbitrary values, it is possible to calculate r2 using Equation 28 or 29 and Equation 33 or 36. When, for example, i2, V2, and r2 are determined to be arbitrary values, it is possible to calculate t2 using Equation 28 or 29 and Equation 32 or 35. When, for example, V2, r2, and t2 are determined to be arbitrary values, it is possible to calculate i2 using Equation 28 or 29 and Equation 34 or 37.

The modification unit 13 then modifies the first imaging condition to the second imaging condition by, among the parameters included in the first imaging condition, changing the value of the parameter received in Step S32 to the arbitrary value, and changing the values of the remaining unreceived parameters to the values calculated in Step S33 (Step S34).

FIG. 11 is a table illustrating examples of the second imaging condition obtained by the modification performed by the modification unit 13.

As described earlier, the first imaging condition for the examinee's body 100 having a thickness of 21 cm and a muscular body build includes a tube voltage of 120 kVp, a tube current of 100 mA, an imaging time of 0.04785 s, and an imaging distance of 200 cm. However, the image capturing is not possible in some cases when the imaging time is 0.04785 s, depending on the x-ray system. For example, when the x-ray system is a system the imaging time for which is changeable at 0.05-s intervals, the standard-body imaging condition modification unit 12 displays, on the display unit, 0.04785 s as the optimal imaging time, for example, and also displays, on the display unit, as candidates for the imaging time to which the imaging time included in the standard-body imaging condition can be changed, 0.045 s and 0.050 s that are parameters closest to 0.04785 s. By doing so, the standard-body imaging condition modification unit 12 prompts the image-capturing person to select an imaging time from these candidates displayed. For example, when 0.045 s is selected, the modification unit 13 displays, to the image-capturing person, 122 kVp obtained by adjusting the tube voltage 120 kVp included in the first imaging condition, using 0.045 s selected as the closest imaging time and the approximate function. As shown above, the standard-body imaging condition modification unit 12 presents, to the image-capturing person, an imaging time closest to the imaging time included in the first imaging condition, and the modification unit 13 presents, to the image-capturing person, a value obtained by adjusting (modifying) the tube voltage included in the first imaging condition, using the closest imaging time and the approximate function, and if there is no problem with the presented value, determines the imaging condition including the presented value, as the second imaging condition. This is how the first imaging condition for the examinee's body 100 is modified to the second imaging condition (Condition 1 illustrated in FIG. 11).

For example, although the x-ray tube having a small focal spot is used in the first imaging condition, we assume here a case where the image-capturing person wishing to take the motion of the examined body part into consideration selects an x-ray tube having a large focal spot, and determines 200 mA, 0.020 s, and 200 cm as arbitrary values for the tube current, the imaging time, and the imaging distance in the first imaging condition, respectively. In this case, since the standard-body imaging condition modification unit 12 has already calculated the converted value (10.662 cm) by converting the thickness of the examinee's body 100 to the phantom thickness, the modification unit 13 obtains, with reference to FIGS. 9, 3.95, 18.911, 0.538, 12.383, and 0.53 as the values of k1, k2, k3, k4, and k5, respectively, that correspond to the closest converted value 11 cm, for example. Then, in order to calculate a new tube voltage, that is, one of the remaining parameters that the image-capturing person did not change to an arbitrary value, the modification unit 13 assigns each numerical value to Equation 31 because Q<1, and displays 127.36 kVp to the image-capturing person as a candidate value for the new tube voltage. Then, when the image-capturing person determines that there is no problem with a new tube voltage of 127 kVp as the value closest to the candidate value for the new tube voltage, the modification unit 13 modifies the first imaging condition to the second imaging condition including this new tube voltage. In other words, the second imaging condition in this case is Condition 2 in FIG. 11.

For example, we assume a case where the image-capturing person, in an attempt to capture an image with an imaging time shorter than the imaging time in the first imaging condition, sets an arbitrary value of 250 mA as the tube current, an arbitrary value of 0.012 s as the imaging time, and an arbitrary value of 150 cm as the imaging distance. In this case, the modification unit 13 assigns each numerical value to Equation 30 because Q>1, and displays 116.77 kVp as a candidate value for the new tube voltage. Then, when the image-capturing person determines that there is no problem with a new tube voltage of 117 kVp as the value closest to the candidate value for the new tube voltage, the modification unit 13 modifies the first imaging condition to Condition 3.

Similarly, when the image-capturing person sets an arbitrary value of 86 kVp as the tube voltage, an arbitrary value of 320 mA as the tube current, and an arbitrary value of 150 cm as the imaging distance, the modification unit 13 assigns each numerical value to Equation 32 because V2<V1, and displays 0.0299 s to the image-capturing person as a candidate value for a new imaging time. Then, when the image-capturing person determines that there is no problem with a new imaging time of 0.032 s as the value closest to the candidate value for the new imaging time, the modification unit 13 modifies the first imaging condition to Condition 4.

Similarly, when the image-capturing person sets an arbitrary value of 77 kVp as the tube voltage, an arbitrary value of 400 mA as the tube current, and an arbitrary value of 0.040 s as the imaging time, the modification unit 13 assigns each numerical value to Equation 33 because V2<V1, and displays 157.08 cm to the image-capturing person as a candidate value for a new imaging distance. Then, when the image-capturing person determines that there is no problem with a new imaging distance of 157 cm as the value closest to the candidate value for the new imaging distance, the modification unit 13 modifies the first imaging condition to Condition 5.

It should be noted that the modification unit 13 may further modify the second imaging condition obtained. The modification unit 13 presents, to the image-capturing person, a parameter value closest to the parameter value included in the second imaging condition, and presents, to the image-capturing person, a value obtained by adjusting the tube voltage included in the second imaging condition, using the closest parameter value and the approximate function. Specifically, with Condition 4, the modification unit 13 presents 0.032 s as the parameter value closest to 0.0299 s that is a candidate value for the new imaging time. The modification unit 13 then presents (displays), to the image-capturing person, a new tube voltage of 84.50 kVp obtained by adjusting the tube voltage included in the second imaging condition using the closest parameter value (0.032 s) and an equation which is based on the approximate function. Condition 4 may be modified to Condition 6 in this manner.

Next, when there is a problematic parameter among the parameters included in the second imaging condition, the modification unit 13 prompts the image-capturing person to change the problematic parameter (Step S35). Description of the problematic parameter will not be repeated as it is the same as in Step S25.

For example, when the mAs value included in the second imaging condition is less than the mAs value predetermined for each examined body part to be imaged and each converted value according to the performance of the x-ray system based on the radiographic mottle, the modification unit 13 prompts the image-capturing person to set the mAs value included in the second imaging condition to a value greater than the predetermined mAs value.

Specifically, from the standpoint of the radiographic mottle, the granularity of the x-ray image deteriorates when, for example, the mAs value is small, due to a small quantity of photons generated. For this reason, the minimum mAs value is determined according to the thickness of the examinee's body (examined body part) to be imaged and the performance of the components included in the x-ray system. Accordingly, the storage unit 11 stores in advance the minimum mAs value corresponding to the performance of the components included in the x-ray system, for example. With this, the modification unit 13 informs the image-capturing person again of the need to modify the second imaging condition, in order to exclude an imaging condition including an extremely small mAs value from the second imaging conditions. For example, the storage unit 11 stores in advance a minimum mAs value according to a restriction such as "the mAs value needs to be 1.5 or greater in the case of imaging the lung fields of the chest and using the anti-scatter device". The modification unit 13 then determines whether or not the mAs value included in the second imaging condition is less than the minimum mAs value, and when the mAs value included in the second imaging condition is less than the minimum mAs value, prompts the image-taking person to change (increase) the mAs value included in the second imaging condition.

Furthermore, for example, when the examined body part to be imaged is the chest and the imaging time included in the second imaging condition exceeds an imaging time predetermined for controlling blur caused by cardiac motion, the modification unit 13 prompts the image-capturing person to set the imaging time included in the second imaging condition to a value not exceeding the predetermined imaging time.

Further, for example, when the examined body part to be imaged is the abdomen and the imaging time included in the second imaging condition exceeds an imaging time predetermined for controlling blur caused by peristalsis motion of gastrointestine, the modification unit 13 prompts the image-capturing person to set the imaging time included in the second imaging condition to a value not exceeding the predetermined imaging time.

Furthermore, for example, when the tube voltage included in the second imaging condition is not within a tube voltage range predetermined for each examined body part to be imaged, based on the anti-scatter standpoint or the anti-scatter device 70 included in the x-ray system used for obtaining an x-ray image, the modification unit 13 prompts the image-capturing person to set the tube voltage included in the second imaging condition to a value within the predetermined tube voltage range.

Moreover, for example, when the tube voltage, the tube current, or the imaging time included in the second imaging condition does not meet the rating of the x-ray system used for obtaining an x-ray image, the modification unit 13 prompts the image-capturing person to set the tube voltage, the tube current, or the imaging time included in the second imaging condition to a value that meets the rating.

In addition, for example, when the tube voltage included in the second imaging condition is not within a tube voltage range predetermined for each examined body part to be imaged, based on the standpoint of the radiographic contrast, the modification unit 13 prompts the image-capturing person to set the tube voltage included in the second imaging condition to a value within the predetermined tube voltage range.

For example, there is an inappropriate combination as a parameter combination, depending on the performance of the anti-scatter device 70 or the rating of the x-ray generation device or of the x-ray tube. Specifically, the SID has usage restrictions depending on the performance of the anti-scatter device. For example, in the case of the x-ray system 1, a tube voltage of 40 kVp is inappropriate for the anti-scatter device 70 that is a 10:1 anti-scatter device for 120 kVp, and the SID is restricted as well. Furthermore, as the rating of the x-ray tube, a tube current of 400 mA is inappropriate when the tube voltage is 120 kVp. In addition, parameter combinations according to the rating of the x-ray tube are restricted, depending also on whether the x-ray tube used has a large focal spot or a small focal spot.

In such a manner, the modification unit 13 can restrict the combinations of the tube voltage, the tube current, and the imaging time and prompt the image-capturing person again to modify the second imaging condition.

In FIG. 11, restrictions are placed on imaging conditions, and imaging conditions that do not meet the restrictions are excluded. The restrictions include, for example, that: the tube voltage is within the tube voltage range from 70 kVp to 140 kVp based on the radiographic contrast of the examined body part and the performance of the anti-scatter device 70; the SID is between 150 cm and 200 cm inclusive based on the anamorphosis of an x-ray image or a request for a real size image and the performance of the anti-scatter device 70; the minimum mAs value needs to be 1.5 or greater from the standpoint of the radiographic mottle; an imaging condition including a tube voltage of 88 kVp or greater cannot be used when a tube current of 320 mA is used, due to the rating of the x-ray system 1; and an imaging condition including a tube voltage of 78 kVp or greater cannot be used when a tube current of 400 mA is used, due to the rating of the x-ray system 1.

Further, for example, when the modification unit 13 has changed, as at least one parameter among parameters included in the first imaging condition, the tube current to, as an arbitrary value, a maximum tube current for the rating based on the size of the focal spot of the x-ray tube included in the x-ray system used for obtaining an x-ray image, and the tube voltage included in the second imaging condition is not within the tube voltage range predetermined based on the anti-scatter device 70 included in the x-ray system and the standpoint of the radiographic contrast, the modification unit 13 gradually decreases the tube current as at least one parameter so that the tube voltage included in the second imaging condition falls within the predetermined tube voltage range. For example, when the first imaging condition is changed such that: the tube voltage is changed to 60 kVp; the tube current is changed to 100 mA that is the maximum tube current for the rating when an x-ray tube having a small focal spot is used; and the imaging time is changed to 0.1 s, and the predetermined tube voltage range is 70 kVp or greater, the modification unit 13 gradually decreases the tube current so that the tube voltage becomes 70 kVp or greater (for example, gradually decreases the tube current from 100 mA so that the tube voltage becomes 70 kVp or greater at a tube current of 50 mA).

Further, for example, when the modification unit 13 has changed, as at least one parameter among parameters included in the first imaging condition, the mAs value to, as an arbitrary value, a minimum mAs value predetermined according to the radiographic mottle and the performance of the x-ray system, and the tube voltage included in the second imaging condition is not within the tube voltage range predetermined based on the anti-scatter device 70 included in the x-ray system used for obtaining an x-ray image and the standpoint of the radiographic contrast, the modification unit 13 gradually increases the mAs value as at least one parameter so that the tube voltage included in the second imaging condition falls within the predetermined tube voltage range. For example, when the first imaging condition is changed such that the tube voltage is changed to 150 kVp and the mAs value is changed to, for instance, 1.5 mAs that is the predetermined minimum mAs value, and the predetermined tube voltage range is 120 kVp or less, the modification unit 13 gradually increases the mAs value so that the tube voltage becomes 120 kVp or less (for example, the tube voltage becomes 120 kVp or less at a mAs value of 3.0 mAs).

Then, for example, by the image-capturing person entering into the operation panel 20 an arbitrary value which the value of a problematic parameter among the parameters included in the second imaging condition is to be changed to, the modification unit 13 changes the value of the problematic parameter to the arbitrary value, and modifies again the second imaging condition based on the first imaging condition using an equation that is based on the arbitrary value and an approximate function.

[Advantageous Effects]

With the conventional exponential method, a tube voltage coefficient table is prepared for each configuration of the x-ray system, and when the tube voltage needs to be changed, the image-capturing person refers to the table and changes the tube voltage to a new tube voltage. This means that, the image-capturing person needs to refer to the table every time he/she makes such a change to the imaging condition that involves a change to the tube voltage, thus making the process extremely inefficient. Moreover, since a roughly calculated value or a round figure is used for convenience as the exponential of the exponential function used for preparing the table, such a roughly calculated exponent causes an error in an exponential operation to increase exponentially. Thus, such a conventional method has been impractical for actual x-ray imaging.

In view of the above circumstances, an x-ray imaging condition modification method according to the present embodiment is an x-ray imaging condition modification method for modifying an imaging condition to obtain an x-ray image having an appropriate radiographic effect using x-rays emitted from an x-ray tube, the imaging condition including, as parameters, at least (i) a tube voltage, (ii-1) a tube current and an imaging time or (ii-2) a mAs value which is a product of the tube current and the imaging time, and (iii) an imaging distance between a focal spot of the x-ray tube and an x-ray detector system. The method includes modifying a first imaging condition to a second imaging condition by changing a value of at least one parameter among the parameters included in the first imaging condition to an arbitrary value, and changing values of remaining parameters that are parameters other than the at least one parameter using the arbitrary value and an approximate function, the second imaging condition being an imaging condition under which an x-ray image having a radiographic effect equivalent to a radiographic effect of an x-ray image obtained under the first imaging condition is obtained. The approximate function is for approximating to a curve obtained by plotting, for each of a plurality of imaging conditions, a relationship between a new tube voltage included in each of the plurality of imaging conditions and a mAs value coefficient Q represented by Equation 22, where i2, t2, and r2 represent a new tube current, a new imaging time, and a new imaging distance, respectively, which are included in the plurality of imaging conditions, and i1, t1, and r1 represent the tube current, the imaging time, and the imaging distance, respectively, which are included in the first imaging condition, the plurality of imaging conditions being determined through an experiment so as to obtain the x-ray image having the radiographic effect equivalent to the radiographic effect of the x-ray image obtained under the first imaging condition.

Furthermore, the x-ray system according to the present embodiment includes: the computer 10 that performs the above-described x-ray imaging condition modification method; the high-voltage generation device 30 that generates the tube voltage and the mAs value corresponding to the second imaging condition obtained by the modification performed by the computer 10; the x-ray tube 40 that emits x-rays at the tube voltage and the mAs value supplied from the high-voltage generation device 30; and the x-ray detector system 50 that detects the x-rays emitted from the x-ray tube 40.

When the image-capturing person wishes to change the value of at least one parameter among the parameters included in the first imaging condition to an arbitrary value, it is necessary to also change the values of the remaining parameters according to the arbitrary value. With the x-ray imaging condition modification method and the x-ray system described above, however, it is possible, using an approximate function, to calculate, as the values of the remaining parameters, values corresponding to the arbitrary value through high-speed computation, and modify the first imaging condition to a second imaging condition under which an x-ray image having a radiographic effect equivalent to the radiographic effect of the x-ray image obtained under the first imaging condition is obtained. It is thus possible to easily modify the first imaging condition to the second imaging condition under which an x-ray image having a radiographic effect equivalent to the radiographic effect of the x-ray image obtained under the first imaging condition is obtained.

The x-ray imaging condition modification method may further include modifying a standard-body imaging condition using a converted value obtained by converting a thickness of an examinee's body into a phantom thickness by taking a body build of the examinee's body into consideration, the standard-body imaging condition being a predetermined imaging condition under which an x-ray image, of a standard body, having an appropriate radiographic effect is obtained. In the modifying of the first imaging condition, a condition obtained by modifying the standard-body imaging condition in the modifying of the standard-body imaging condition is used as the first imaging condition and modified to the second imaging condition. The first imaging condition is an imaging condition for the examinee's body, under which an x-ray image having a radiographic effect equivalent to the radiographic effect of the x-ray image obtained under the standard-body imaging condition is obtained.

With this, it is possible to modify, through high-speed computation using the converted value, the predetermined standard-body imaging condition to the first imaging condition under which an x-ray image having a radiographic effect equivalent to the radiographic effect of the x-ray image obtained under the standard-body imaging condition is obtained.

When $V2 \leq V1$ or when $Q \geq 1$, the approximate function may be represented by Equation 24, and when $V2 > V1$ or when $Q < 1$, the approximate function may be represented by Equation 25, where $Y(V2)$ represents the approximate function, V2 represents the new tube voltage, V1 represents the tube voltage included in the first imaging condition, and k1, k2, k3, k4, and k5 represent values predetermined according to (i) a configuration of an x-ray system used for obtaining an x-ray image, (ii) an examined body part to be imaged, and (iii) the converted value.

With this, it is possible to calculate, as the values of the remaining parameters of the first imaging condition, values corresponding to the arbitrary value through high-speed computation, by using Equation 24 or Equation 25 as the approximate function.

CONCLUSION

There are unique differences in the device performance depending on the x-ray system used. Moreover, there are also unique differences in the device performance depending on whether or not the x-ray system used includes the anti-scatter device and the type of the anti-scatter device if the x-ray system includes the anti-scatter device.

When obtaining an image of an examinee's body that makes motions, the image-capturing person, for example, stores in advance, in a storage unit of the x-ray system, an imaging condition for a standard body (a standard-body imaging condition) for each configuration of the x-ray system and each examined body part. The image-capturing person also stores in advance, in the storage unit of the x-ray system, equations (for example, Equation 9, Equation 13, and Equation 14) used for converting the examinee's body thickness into a phantom thickness by taking the examinee's body build into consideration, and equations (for example, Equation 8, Equation 11, and Equation 12) used for calculating a mAs value from the converted value. The computer then modifies the imaging condition for the standard body (the standard-body imaging condition) to the first imaging condition.

Furthermore, for example, the image-capturing person stores in advance, in the storage unit of the x-ray system, values (k1 to k5) to be included in an approximate function so that an actually-measured graph of a curve showing a relationship between the mAs value coefficient and the new tube voltage can be represented by the approximate function for each configuration of the x-ray system, each examined body part, and each converted value.

After the standard-body imaging condition is modified to the first imaging condition, the image-capturing person enters into the x-ray system (for example, the operation panel) an arbitrary value which the value of at least one parameter among the parameters included in the first imaging condition is to be changed to, when the image-capturing person feels that further modification is necessary from the standpoint of the motion of the examined body part or the magnification ratio, for example. The computer then obtains the configuration of the x-ray system, the examined body part, and the converted value from the storage unit, and determines an approximate function using the values (k1 to k5) to be included in an approximate function corresponding to the configuration of the x-ray system, the examined body part, and the converted value that are obtained. Then, the computer solves an equation which is based on the approximate function, so as to modify the first imaging condition to the second imaging condition under which an x-ray image having a radiographic effect equivalent to the radiographic effect of the x-ray image obtained under the first imaging condition is obtained.

In the modification of an imaging condition to the first imaging condition or the second imaging condition, restrictions according to the standpoint of the radiographic contrast and the radiographic mottle are placed on the tube voltage and the mAs value included in the imaging condition, depending on the configuration of the x-ray system or the examined body part, and restrictions according to the device rating and parameter combinations are also placed. By placing such restrictions, it is possible to narrow down combinations of imaging conditions under which an x-ray image having an equivalent radiographic effect is obtained. This, as a result, makes the modification efficient.

For example, the image-capturing person need not use the imaging condition obtained by the modification performed by the computer. In this case, in the modification, an imaging condition may be received from the image-capturing person, and the image-capturing person may be alerted to unintended exposure when the difference between the mAs value included in the received imaging condition and the mAs value included in the second imaging condition calculated using, as an arbitrary value, the tube voltage in the received imaging condition is greater than a predetermined difference. That is to say, since the imaging condition obtained by the modification performed by the computer need not be used, the image-capturing person can freely determine an imaging condition. At this time, for example, when the image-capturing person makes an error, by one digit, in the value of the parameter pertaining to the mAs value among the parameters of the imaging condition and thus mistakenly sets a large value, the computer can make a comparison between the calculated mAs value and the mAs value determined by the image-capturing person, if the computer has also performed recalculation using the tube voltage set by the image-capturing person. In view of this, if a difference of ±500% of the computer-calculated mAs value is set as being allowable as the predetermined difference, the image-capturing person can be alerted to unintended exposure when an error is made by one digit, because the error by one digit is a difference of 1000%.

As the future prospects, it will be possible to easily modify the standard-body imaging condition to the first imaging condition if the x-ray system includes a sensor capable of detecting the examinee's body thickness and body build from the external appearance of the examinee's body. Further, it will be possible to easily determine a magnification ratio if the sensor detects the position of the x-ray tube and the position of the x-ray detector system and the image-capturing person notifies the x-ray system of the position of the examined body part. Furthermore, if the sensor detects the amount of motion of the examinee's body, the computer can automatically narrow down imaging conditions further, and it will be possible to obtain an x-ray image of the examinee's body having an appropriate radiographic effect, without being influenced by the skill and knowledge of the image-capturing person.

(Other Embodiments)

An x-ray imaging condition modification method and an x-ray system according to the present disclosure have been described above based on the above embodiment. The present disclosure, however, is not limited to the above embodiment.

For example, general or specific aspects of the present disclosure may be realized using a system, a method, an integrated circuit, a computer program, or a computer-readable recording medium such as a CD-ROM. For example, the present disclosure may be realized as a program for causing a computer to perform the x-ray imaging condition modification method described above.

The program may be integrated into the x-ray system. This is because the mAs value coefficient is common if identical x-ray systems or x-ray systems of the same type are used, and there is no need to prepare the mAs value coefficient through an experiment for each x-ray system. In addition, it is unnecessary for the image-capturing person to know the values (k1 to k5) to be included in an approximate function determined for each configuration of the x-ray system, each examined body part, and each converted value, and when the image-capturing person changes a part of the parameters of the imaging condition, it is only necessary for the computer to automatically change the remaining parameters. With this, the x-ray system maintains to be a black box.

Furthermore, for example, although the x-ray system in the above embodiment includes the standard-body imaging condition modification unit 12, the x-ray system need not include the standard-body imaging condition modification unit 12. To put it differently, the x-ray imaging condition modification method and the program thereof need not include the modification of the standard-body imaging condition before the modification of the first imaging condition. In this case, the first imaging condition need not be an imaging condition obtained by the modification performed by the standard-body imaging condition modification unit 12. That is to say, the present disclosure makes it possible to modify the first imaging condition to the second imaging condition which is different from the first imaging condition and under which an x-ray image having a radiographic effect equivalent to the radiographic effect of the x-ray image obtained under the first imaging condition is obtained.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

The invention claimed is:

1. An x-ray imaging condition modification method for modifying an imaging condition to obtain an x-ray image having an appropriate radiographic effect using x-rays emitted from an x-ray tube, the imaging condition including, as parameters, at least (i) a tube voltage, (ii-1) a tube current and an imaging time, or (ii-2) an mAs value which is a product of the tube current and the imaging time, and (iii) an imaging distance between a focal spot of the x-ray tube and an x-ray detector system, the x-ray imaging condition modification method comprising:

modifying a first imaging condition to a second imaging condition by changing a value of at least one parameter among the parameters included in the first imaging condition to an arbitrary value, and changing values of remaining parameters that are parameters other than the at least one parameter using the arbitrary value and an approximate function, the second imaging condition being an imaging condition under which an x-ray image having a radiographic effect equivalent to a radiographic effect of an x-ray image obtained under the first imaging condition is obtained, wherein the approximate function is for approximating to a curve obtained by plotting, for each of a plurality of imaging conditions, a relationship between a new tube voltage included in each of the plurality of imaging conditions and an mAs value coefficient Q represented by:

$$Q = \frac{(i2)(t2)}{(r2)^2} \frac{(r1)^2}{(i1)(t1)} \qquad [\text{Math. 1}]$$

where i2, t2, and r2 represent a new tube current, a new imaging time, and a new imaging distance, respectively, which are included in the plurality of imaging conditions, and i1, t1, and r1 represent a tube current, an imaging time, and an imaging distance, respectively, which are included in the first imaging condition, the plurality of imaging conditions being determined through an experiment so as to obtain the x-ray image having the radiographic effect equivalent to the radiographic effect of the x-ray image obtained under the first imaging condition.

2. The x-ray imaging condition modification method according to claim 1, further comprising:

modifying a standard-body imaging condition to obtain a condition using a converted value obtained by converting a thickness of an examinee's body into a phantom thickness by taking a body build of the examinee's body into consideration, the standard-body imaging condition being a predetermined imaging condition under which an x-ray image, of a standard body, having an appropriate radiographic effect is obtained, wherein the modifying of the first imaging condition to the second image condition further comprises using the condition as the first imaging condition, and wherein the first imaging condition is an imaging condition for the examinee's body, under which an x-ray image having a radiographic effect equivalent to the radiographic effect of the x-ray image obtained under the standard-body imaging condition is obtained.

3. The x-ray imaging condition modification method according to claim 2, wherein when V2≤V1 or when Q ≥1, the approximate function is represented by:

[Math. 2]

$$Y(V2) = \frac{\exp(k2)}{(V2)^{k1}},$$

and when V2>V1 or when Q <1, the approximate function is represented by:

$$Y(V2) = \exp(-(V2)^{k3} + k4) + k5 \qquad [\text{Math. 3}]$$

where Y(V2) represents the approximate function, V2 represents the new tube voltage, V1 represents the tube voltage included in the first imaging condition, and k1, k2, k3, k4, and k5 represent values predetermined according to (i) a configuration of an x-ray system used for obtaining an x-ray image, (ii) an examined body part to be imaged, and (iii) the converted value.

4. An x-ray system, comprising:

a computer that performs the x-ray imaging condition modification method according to claim 1;

a high-voltage generation device that generates a tube voltage and an mAs value that correspond to the second imaging condition;

an x-ray tube that emits x-rays at the tube voltage and the mAs value generated by the high-voltage generation device; and an x-ray detector system that detects the x-rays emitted from the x-ray tube.

* * * * *